(12) United States Patent
Guenther et al.

(10) Patent No.: US 8,109,934 B2
(45) Date of Patent: Feb. 7, 2012

(54) ALL THROUGH ONE DRILL GUIDE FOR CERVICAL PLATING

(75) Inventors: Kevin V. Guenther, Carver, MN (US); Jason S. Piehl, Apple Valley, MN (US); Leanne B. Dittmer, Plymouth, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1328 days.

(21) Appl. No.: 11/281,777

(22) Filed: Nov. 16, 2005

(65) Prior Publication Data
US 2006/0189997 A1 Aug. 24, 2006

Related U.S. Application Data

(60) Provisional application No. 60/652,052, filed on Feb. 10, 2005.

(51) Int. Cl.
*A61B 17/58* (2006.01)
(52) U.S. Cl. .......... 606/96; 606/86 B; 606/914; 606/916
(58) Field of Classification Search .......... 606/104, 606/280, 281, 96, 97, 98, 99, 915, 914, 282–299, 606/70, 71, 86 A, 86 B, 105, 90, 916; 81/44, 81/451, 462
See application file for complete search history.

(56) References Cited

U.S. PATENT DOCUMENTS

| | | | |
|---|---|---|---|
| 4,465,065 A | 8/1984 | Gotfried | |
| 5,180,388 A | 1/1993 | DiCarlo | |
| 5,306,278 A | 4/1994 | Dahl et al. | |
| 5,364,399 A | 11/1994 | Lowery et al. | |
| 5,423,826 A | 6/1995 | Coates et al. | |
| 5,531,751 A | 7/1996 | Schultheiss et al. | |
| 5,669,915 A | 9/1997 | Caspar et al. | |
| 5,676,666 A | 10/1997 | Oxland et al. | |
| 5,741,266 A * | 4/1998 | Moran et al. | 606/96 |
| 5,755,721 A | 5/1998 | Hearn | |
| 5,769,856 A | 6/1998 | Dong et al. | |
| 5,851,207 A | 12/1998 | Cesarone | |
| 5,899,908 A | 5/1999 | Kuslich et al. | |
| 6,059,789 A | 5/2000 | Dinger et al. | |

(Continued)

OTHER PUBLICATIONS

ACLP™ —Anterior Cervical Locking Plate System Technique Guide, Synthes Spine, Paoli, PA, Title pages, Table of Contents, and pp. 2-19 (19 pages total) (Nov. 2003).

*Primary Examiner* — Eduardo C Robert
*Assistant Examiner* — Jan Christopher Merene
(74) *Attorney, Agent, or Firm* — Seager Tufte & Wickhem LLC

(57) ABSTRACT

Embodiments of the present invention provide apparatus for guiding medical instruments, including a handle with a handle shaft, an alignment stand configured to interface with a receptacle of a cervical plate, an instrument guide tube coupled to the alignment stand and having a lumen therethrough, such that when the alignment stand is in communication with the receptacle, the instrument guide tube is positioned over a bone screw receiving hole in the cervical plate and an axial centerline of the instrument guide tube passes through the bone screw receiving hole. Instrument guide tube may swivel about the alignment stand via a rotational coupling, or may be one of two fixed instrument guide tubes. Alignment stand may include an angle-limiting post to interface with the receptacle to permit ranges of tilting, or a stem and optional bone pin for holding the alignment stand at a substantially constant angle in the receptacle.

12 Claims, 39 Drawing Sheets

U.S. PATENT DOCUMENTS

| | | | |
|---|---|---|---|
| 6,066,142 | A | 5/2000 | Serbousek et al. |
| 6,193,721 | B1 | 2/2001 | Michelson |
| 6,235,034 | B1 | 5/2001 | Bray |
| D449,692 | S | 10/2001 | Michelson |
| 6,342,056 | B1 | 1/2002 | Mac-Thiong et al. |
| 6,342,057 | B1 | 1/2002 | Brace et al. |
| 6,379,364 | B1 | 4/2002 | Brace et al. |
| 6,398,783 | B1 | 6/2002 | Michelson |
| 6,416,528 | B1 | 7/2002 | Michelson |
| 6,454,771 | B1 | 9/2002 | Michelson |
| 6,592,586 | B1 * | 7/2003 | Michelson ............ 606/71 |
| 6,692,503 | B2 | 2/2004 | Foley et al. |
| 7,011,665 | B2 * | 3/2006 | Null et al. ............ 606/99 |
| 2002/0045896 | A1 * | 4/2002 | Michelson ............ 606/61 |
| 2002/0147450 | A1 | 10/2002 | LeHuec et al. |
| 2002/0156481 | A1 | 10/2002 | Boyd et al. |
| 2003/0083667 | A1 | 5/2003 | Ralph et al. |
| 2004/0015174 | A1 | 1/2004 | Null et al. |
| 2005/0015093 | A1 * | 1/2005 | Suh et al. ............ 606/96 |
| 2005/0228400 | A1 * | 10/2005 | Chao et al. ............ 606/104 |
| 2006/0155284 | A1 * | 7/2006 | Doherty et al. ........ 606/69 |
| 2008/0154280 | A1 * | 6/2008 | Schumacher et al. .... 606/104 |

* cited by examiner

ALL THROUGH ONE DRILL GUIDE FOR CERVICAL PLATING

CROSS-REFERENCE TO RELATED APPLICATIONS

The present application claims the benefit of U.S. Provisional Patent Application No. 60/652,052, entitled "All Through One Drill Guide for Cervical Plating" and filed on Feb. 10, 2005. The aforementioned application is hereby incorporated by reference herein in its entirety for all purposes.

BACKGROUND OF THE INVENTION

1. Field

The present invention relates generally to medical instrument guide devices, and more particularly to instrument guide devices for guiding cervical plating attachment instruments.

2. Description of Related Art

When medical professionals need to perform a task such as drilling, tapping, or screwing into bone, it is often beneficial for the hole, threads, or screw to be straight and for the drilling, tapping, and/or screwing tool to reduce excess lateral pressure to the bone that could weaken or break the bone around the hole. For example, when drilling, tapping, or screwing in order to attach a cervical plate to underlying bone, the holes should be straight into the bone at an angle that promotes solid attachment.

Early solutions for attaching a cervical plate to underlying vertebrae involved drilling, tapping, and/or screwing without any guide. Without a guide, the surgeon had to maintain a particularly steady hand and had to rely on judging the angle of entry with the naked eye. Eventual solutions involved drilling and tapping a hole through a guide, then removing the guide and screwing the screw into the hole by hand or without the aid of a guide.

More recent guides include both single- and double-barreled guides. These guide solutions, however, use the guide barrels themselves to stabilize the guides on or over the cervical plate. Such solutions provide limited stabilization. In addition, these prior solutions do not control the angle at which holes can be made relative to the cervical plate. As a result, holes often will be made while the guide barrels extend from the cervical plate at angles that are too caudad or too cephalad. Further, prior single-barreled guide designs often necessitate two or more separately-manufactured guides to be used for different bone screw holes of the cervical plate, and often required one single-barreled guide to be inserted after another, or the same single-barreled guide to be lifted from the cervical plate and positioned over another bone screw hole.

Thus, there is a need for improved instrument guide devices for attaching cervical plates to underlying vertebrae.

BRIEF SUMMARY OF THE INVENTION

Some embodiments of the present invention provide an apparatus for guiding medical instruments, including a handle with a handle shaft, an alignment stand affixed to the handle shaft and configured to interface with a receptacle in a cervical plate, and an instrument guide tube coupled to the alignment stand and having a lumen therethrough. According to such embodiments, when a first end of the alignment stand is in communication with the receptacle in the cervical plate, the instrument guide tube is positioned over a bone screw receiving hole in the cervical plate and an axial centerline of the instrument guide tube passes through the bone screw receiving hole. The instrument guide tube may include a first end with a depth stop collar, and a second end that is tapered. The cervical plate may include a locking cap which acts as the receptacle.

In some cases, the first end of the alignment stand includes an angle-limiting post configured to permit the alignment stand to interface with the receptacle at a varying angle. The angle-limiting post may limit the varying angle by abutting the receptacle when the varying angle equals a maximum angle. In other cases, the alignment stand includes a stem configured to hold the alignment stand at a substantially constant angle with respect to the receptacle. The alignment stand may further include a bone pin configured to pass through a fixation hole of the cervical plate and into the bone of a vertebral body to hold the cervical plate to the bone during use of the apparatus.

The instrument guide tube may be coupled to a second end of the alignment stand. In some instances, the instrument guide tube can swivel about the alignment stand so that instrument guide tube stand can be positioned over a second bone screw receiving hole in the cervical plate. In other instances, the instrument guide tube is a first instrument guide tube, and the bone screw receiving hole is a first bone screw receiving hole, and embodiments of the apparatus may further include a second instrument guide tube coupled to the alignment stand and including a lumen therethrough. In such instances, the alignment stand may be configured to interface with the receptacle of the cervical plate, such that when the first end of the alignment stand is in communication with the receptacle in the cervical plate, the second instrument guide tube is positioned over a second bone screw receiving hole in the cervical plate and an axial centerline of the second instrument guide tube passes through the second bone screw receiving hole.

Some embodiments of the present invention provide an apparatus for guiding medical instruments, the apparatus including a handle comprising a handle shaft, an alignment stand affixed to the handle shaft and configured to interface with a receptacle in a cervical plate, the alignment stand including at least two alignment slots formed therein, and an instrument guide tube including a lumen therethrough and a rotational coupling operable to rotatably couple the instrument guide tube to the alignment stand. The rotational coupling may include an alignment pin operable to seat in one of the at least two alignment slots to prevent the instrument guide tube from rotating about the alignment stand. According to such embodiments, when a first end of the alignment stand is in communication with the receptacle in the cervical plate and the alignment pin is seated in one of the at least two alignment slots, the instrument guide tube is positioned over a bone screw receiving hole in the cervical plate and an axial centerline of the instrument guide tube passes through the bone screw receiving hole.

In some cases, the alignment stand includes a first annular ring and a second annular ring and the at least two alignment slots are formed in the first annular ring. The rotational coupling of the instrument guide tube may include a rotational sleeve surrounding the first and the second annular rings of the alignment stand, the alignment pin may protrude within the rotational sleeve between the first annular ring and the second annular ring, and the rotational sleeve may rotate with respect to the alignment stand unless the alignment pin is seated in one of the at least two alignment slots. The rotational sleeve may include a bottom collar, and the apparatus may further include a spring in compression between the first annular ring and the bottom collar, wherein compression pressure from the spring is operable to hold the alignment pin in the one of the at least two alignment slots, and wherein the spring is operable to further compress as the rotational sleeve is lifted and rotated to permit the alignment pin to seat in another of the at least two alignment slots.

According to some instances of the embodiments, the instrument guide tube includes a first end and a second end, and the first end of the instrument guide tube includes a depth stop collar. The second end of the instrument guide tube may include a taper. In some cases, the first end of the alignment stand includes an angle-limiting post configured to permit the alignment stand to interface with the receptacle at a varying angle, and the angle-limiting post limits the varying angle by abutting the receptacle when the varying angle equals a maximum angle. In other cases, the first end of the alignment stand includes a stem configured to hold the alignment stand at a substantially constant angle with respect to the receptacle. In such cases, the alignment stand may further include a bone pin configured to pass through a fixation hole of the cervical plate and into the bone of a vertebral body to hold the cervical plate to the bone during use of the apparatus.

Some embodiments of the present invention provide an apparatus for guiding medical instruments, the apparatus including a handle with a handle shaft, an alignment stand affixed to the handle shaft and configured to interface with a receptacle in a cervical plate, a first instrument guide tube coupled to the alignment stand and having a lumen therethrough, and a second instrument guide tube coupled to the alignment stand and having a lumen therethrough. According to such embodiments, when a first end of the alignment stand is in communication with the receptacle in the cervical plate, the first instrument guide tube is positioned over a first bone screw receiving hole in the cervical plate and an axial centerline of the first instrument guide tube passes through the first bone screw receiving hole and the second instrument guide tube is positioned over a second bone screw receiving hole in the cervical plate and an axial centerline of the second instrument guide tube passes through the second bone screw receiving hole.

In some cases, the first and the second instrument guide tubes each comprise a first end and a second end, and the first end of the instrument guide tubes includes a depth stop collar. The second end of the instrument guide tubes may be tapered. The cervical plate may include a locking cap which acts as the receptacle.

According to some instances of the embodiments, the first end of the alignment stand includes an angle-limiting post configured to permit the alignment stand to interface with the receptacle at a varying angle. The angle-limiting post may limit the varying angle by abutting the receptacle when the varying angle equals a maximum angle. In other instances, the first end of the alignment stand includes a stem configured to hold the alignment stand at a substantially constant angle with respect to the receptacle. In such instances, the alignment stand may further include a bone pin configured to pass through a fixation hole of the cervical plate and into the bone of a vertebral body to hold the cervical plate to the bone during use of the apparatus. In yet other instances, the first and the second instrument guide tubes are coupled to a second end of the alignment stand.

This summary provides only a general outline of some embodiments of the present invention. Many other objects, features, advantages and other embodiments of the present invention will become more fully apparent from the following detailed description, the appended claims and the accompanying drawings.

BRIEF DESCRIPTION OF THE SEVERAL VIEWS OF THE DRAWINGS

A further understanding of the various embodiments of the present invention may be realized by reference to the figures which are described in remaining portions of the specification. In the figures, like reference numerals are used throughout several to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

Various embodiments of the present invention will now be described with regard to the accompanying drawings which assist in illustrating various features of the invention. In this regard, embodiments of the present invention provide guides for medical instruments. In particular, embodiments of the present invention provide single- or double-barreled, variable-angle or fixed, instrument guide devices for use with tools for securing a cervical plate to underlying vertebrae.

Several different exemplary embodiments of instrument guide devices are generally illustrated in the accompanying FIGS. 1 through 35, which are provided merely for the purpose of illustrating exemplary embodiments disclosed herein. It should be appreciated that these FIGS. are presented only for illustrative purposes and do not constitute limitations on the scope of the present invention. Further, the embodiments disclosed herein are merely exemplary embodiments, and thus, the present invention is not limited to these particular embodiments.

Figure 1:
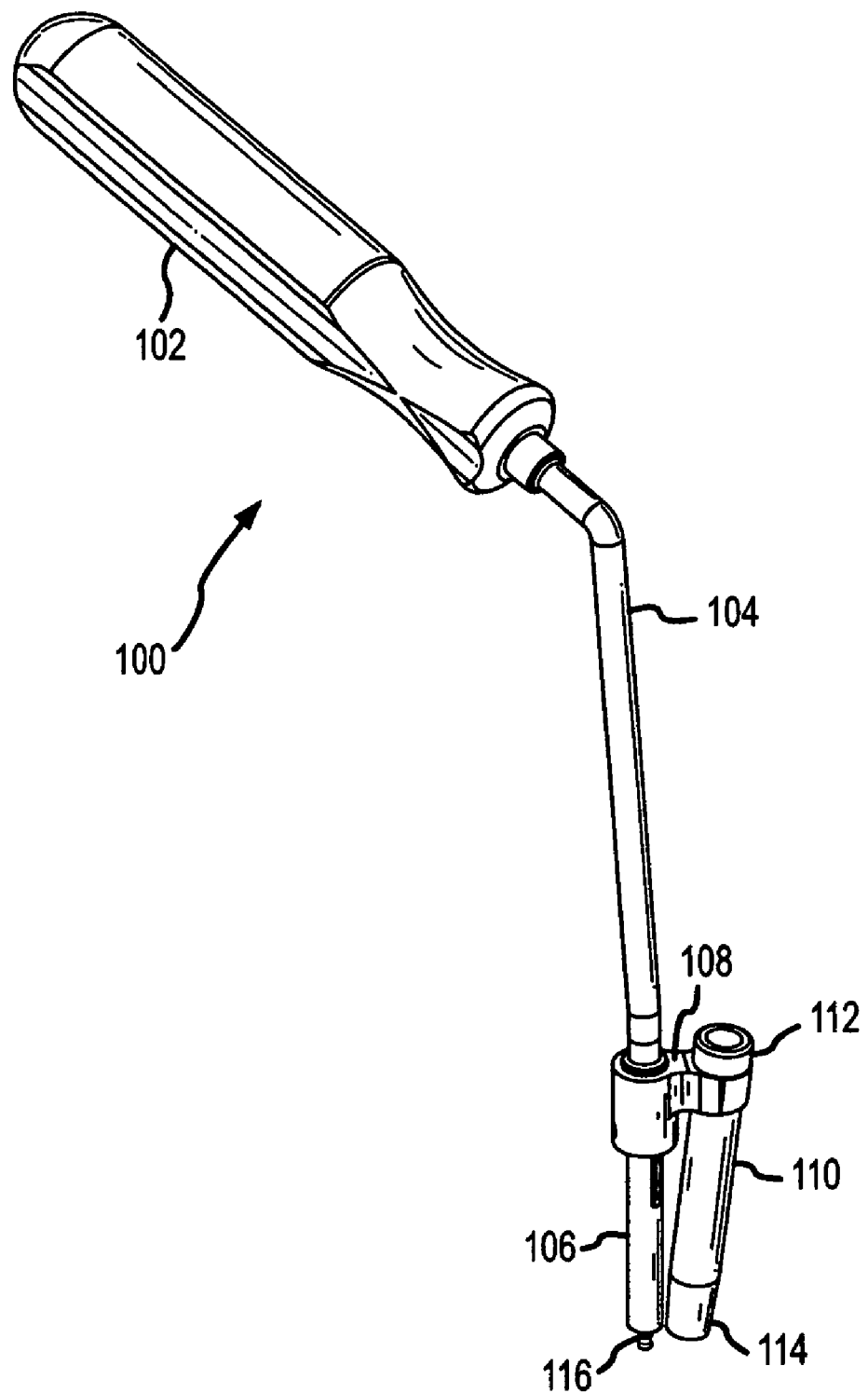
FIG. 1 illustrates an isometric view of an instrument guide device having a swiveling single instrument guide tube according to some embodiments of the present invention.

Referring now to FIG. 1, an instrument guide device 100 having a swiveling single instrument guide tube according to some embodiments of the present invention are illustrated. Instrument guide device 100 includes a handle 102 and a handle shaft 104 for holding instrument guide device 100. In some embodiments of the present invention, handle 102 may be removable from handle shaft 104. An alignment stand 106 is attached to handle shaft 104 and configured to interface with a receptacle in a cervical plate via angle limiting post 116. For example, in some embodiments, alignment stand 106 can interface with a locking cap in a cervical plate, as discussed in more detail below. A rotational coupling 108 interfaces with and/or encompasses a top end of alignment stand 106. An instrument guide tube 110 having a lumen therein is affixed to rotational coupling 108.

According to some embodiments of the present invention, rotational coupling 108 can be spring-loaded to hold instrument guide tube 110 in one of two or more positions, such as, for example, positions over two or more bone screw receiving holes in cervical plate. In addition, instrument guide tube 110 can include a depth stop collar 112 at a top end for contacting and stopping instruments that have been inserted a predetermined depth into instrument guide tube 110. Instrument guide tube 110 also can include a tapered end 114.

Figure 2:
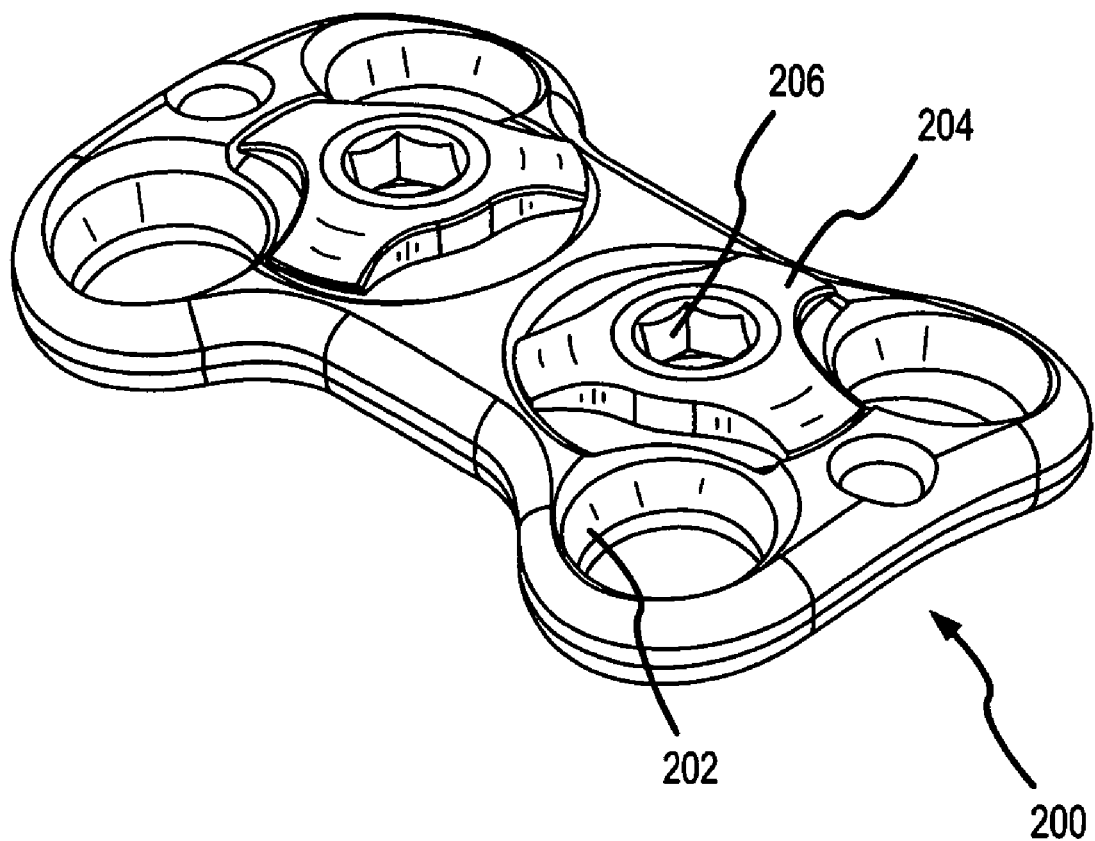
FIG. 2 illustrates an isometric view of one embodiment of a cervical plate according to various embodiments of the present invention.

Referring now to FIG. 2, one embodiment of a cervical plate 200 is shown. In general, cervical plates are known in the art and are configured to be positioned along a midline of vertebral bodies and affixed to the vertebral bodies via bone screws to bridge one or more vertebral bodies, for example. Cervical plate 200 represents one of several different sizes and configurations of cervical plates. In the illustrated embodiment, cervical plate 200 includes two sets of two bone screw receiving holes 202, but other embodiments of cervical plate 200 can have, for example, three or four sets of bone screw receiving holes 202. In addition, in the illustrated embodiment, cervical plate 200 includes a locking cap 204, which has a hex hole 206 for engaging locking cap 204. Various other embodiments of cervical plate 200 are described in greater detail in U.S. Pat. Nos. 6,193,721; 6,398,783; 6,416,528, 6,454,771; and D449,692; the contents of which are incorporated by reference herein in their entirety for all purposes.

Figure 3:
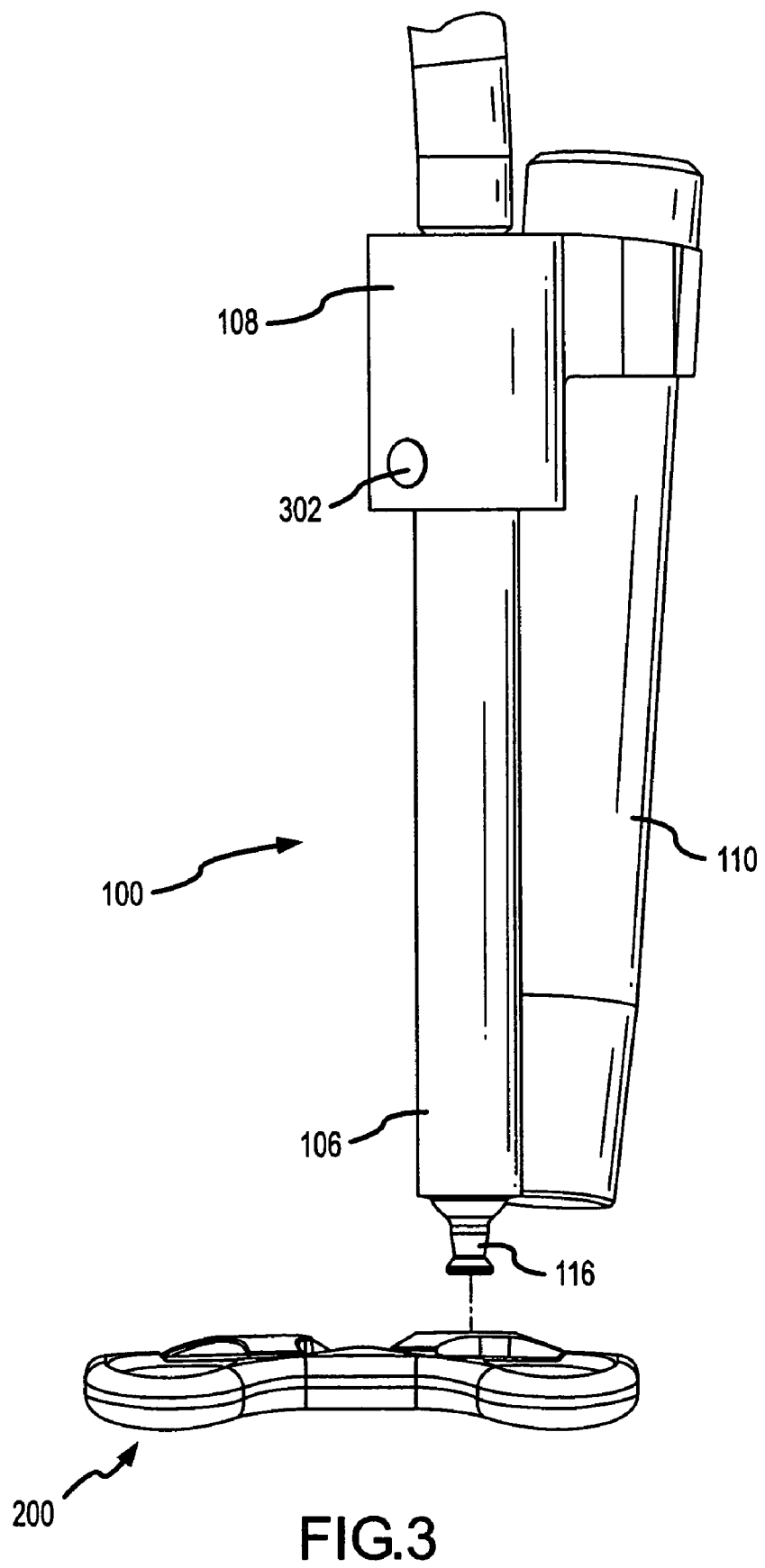
FIG. 3 illustrates an isometric view of an embodiment of the instrument guide device of FIG. 1 in spaced relation with one embodiment of a cervical plate according to various embodiments of the present invention.

Referring now to FIG. 3, an instrument guide device having a swiveling single instrument guide tube 110 is shown positioned above a cervical plate 200, according to some embodiments of the present invention. As illustrated in FIG. 3, rotational coupling 108 includes an alignment pin 302, which is operable to seat within alignment slots (not pictured) on alignment stand 106, thus locking rotational coupling 108 and/or instrument guide tube 110 in one of two or more positions. In addition, instrument guide device 100 can include a clean-out hole 304a formed through rotational coupling 108, allowing the inside of rotational coupling 108 to be seen and/or permitting an area inside of rotational coupling 108 to be cleaned.

Figure 4:
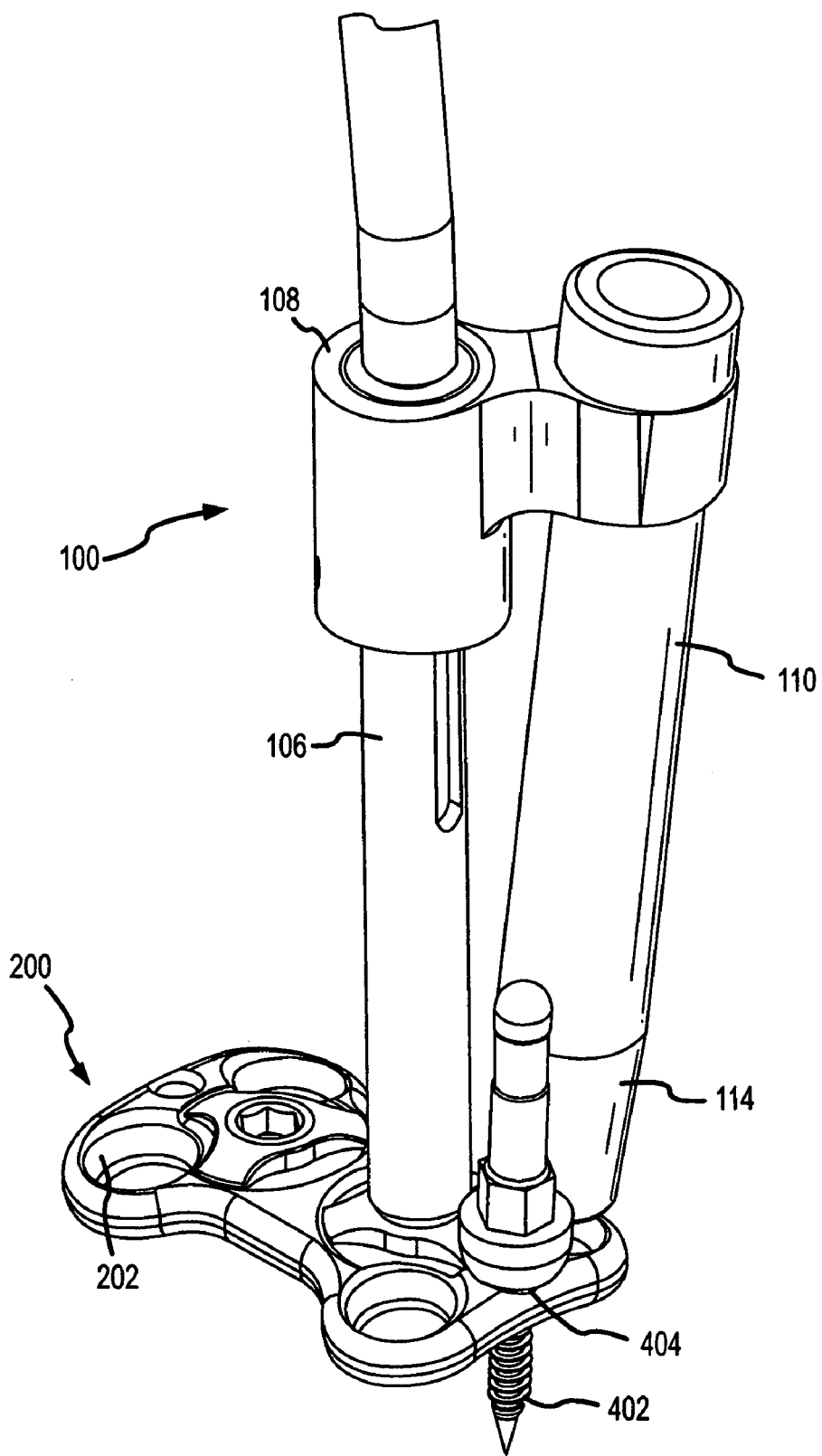
FIG. 4 illustrates an isometric view of the instrument guide device of FIG. 1 in communication with one embodiment of a cervical plate according to various embodiments of the present invention.
Figure 5:
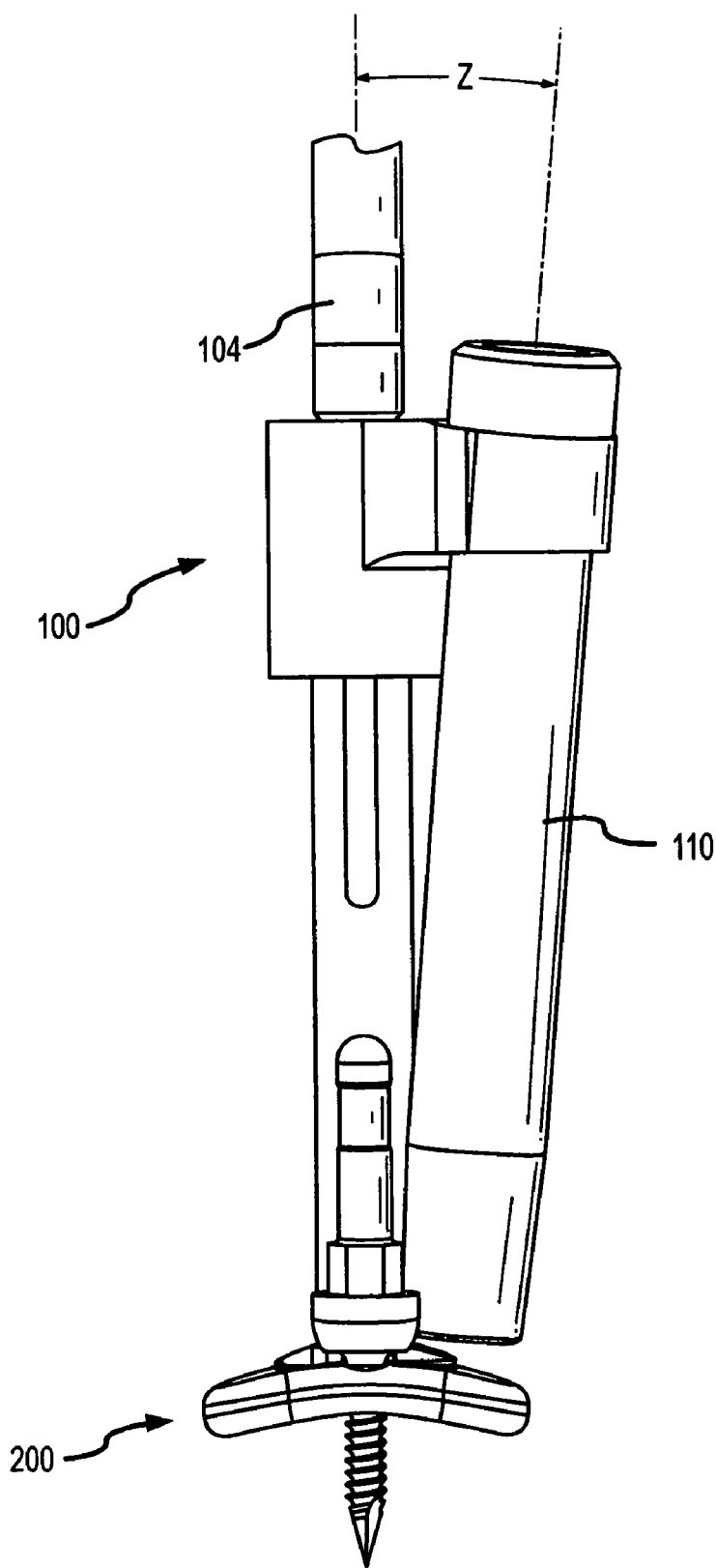
FIG. 5 illustrates a front perspective view of the configuration of FIG. 4.
Figure 6:
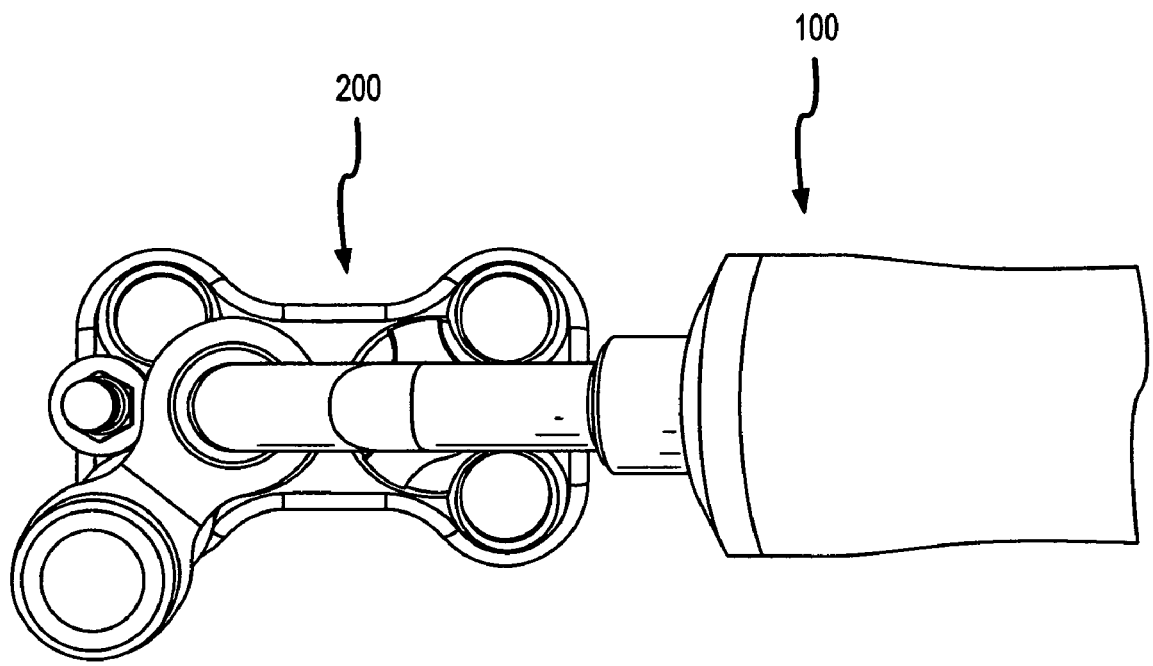
FIG. 6 illustrates a top perspective view of the configurations in FIGS. 4 and 5.

In a common scenario, a cervical plate 200 of an appropriate size is selected for fixation to vertebral bodies. A properly sized plate 200 bridges affected segment(s) without overhanging into the adjacent disc space(s). Cervical plate 200 is positioned on the midline of the vertebral bodies. Referring now to FIGS. 4-6, a fixation pin 402 may be applied through a fixation hole 404 formed within cervical plate 200; fixation pin 402 may operate to hold cervical plate 200 in place during the fixation process: i.e., during drilling, tapping, and/or screwing. For example, fixation pin 402 may be used to hold cervical plate 200 positioned on midline of vertebral bodies during drilling and tapping of the first hole and/or application of the first bone screw through bone screw receiving hole 202 and into the first hole. According to some embodiments of the present invention, fixation pin 402 is used only temporarily to hold cervical plate 200 in place.

Once cervical plate 200 is positioned properly, angle-limiting post 116 of instrument guide device 100 is inserted into hex hole 206 of locking cap portion 204 of cervical plate 200. Handle shaft 104 is then aligned approximately over the midline of cervical plate 200, as depicted in FIGS. 5 and 6, to avoid drilling or placing screws too far medially or laterally. When alignment stand 106 has been inserted into locking cap portion 204, and when rotational coupling 108 and/or instrument guide tube 110 has been locked into one of two or more positions, instrument guide tube 110 is positioned over bone screw receiving hole 202 and an axial center line of instrument guide tube 110 passes through bone screw receiving hole 202, as depicted, for example, in FIGS. 4-6. Tapered end 114 of instrument guide tube 110 may hover over bone screw receiving hole 202; alternatively, tapered end 114 of instrument guide tube 110 may fit on or within bone screw receiving hole 202 when angle-limiting post 116 is inserted into hex hole 206. Alternatively, end 114 may be non-tapered and/or flared. In addition, while the present embodiment has been described with reference to angle-limiting post 116 being positioned within hex hole 206 of locking cap portion 204, the present invention is not limited to this embodiment. In alternative embodiments, cervical plate 200 might include an alternative or additional receptacle for receiving angle-limiting post 116.

According to some embodiments of the present invention, instrument guide tube 110 may be connected to rotational coupling 108 at an angle with respect to the axial centerline of rotational coupling 108; such an angle is similar to the angle between the vertical projection of the midline of cervical plate 200 and the axial centerline of instrument guide tube 110 when handle shaft 104 and alignment stand 106 have been aligned over midline of cervical plate 200, as illustrated in the front view of FIG. 5 and top view of FIG. 6. For example, such an angle may be an angle Z. Angle Z may range from, for example, zero to twelve degrees; in some embodiments, angle Z is equal to approximately six degrees.

A wide range of configurations of instrument guide tube 110 are possible that permit an axial centerline of instrument guide tube 110 to pass through a bone screw receiving hole 202 of cervical plate 200 when alignment stand 106 is inserted into locking cap portion 204. The proximal ends of instrument guide tubes of FIGS. 20 and 29, described below, may be similarly angled inward with respect to an axial centerline of an alignment post, according to some embodiments of the present invention.

Figure 7:
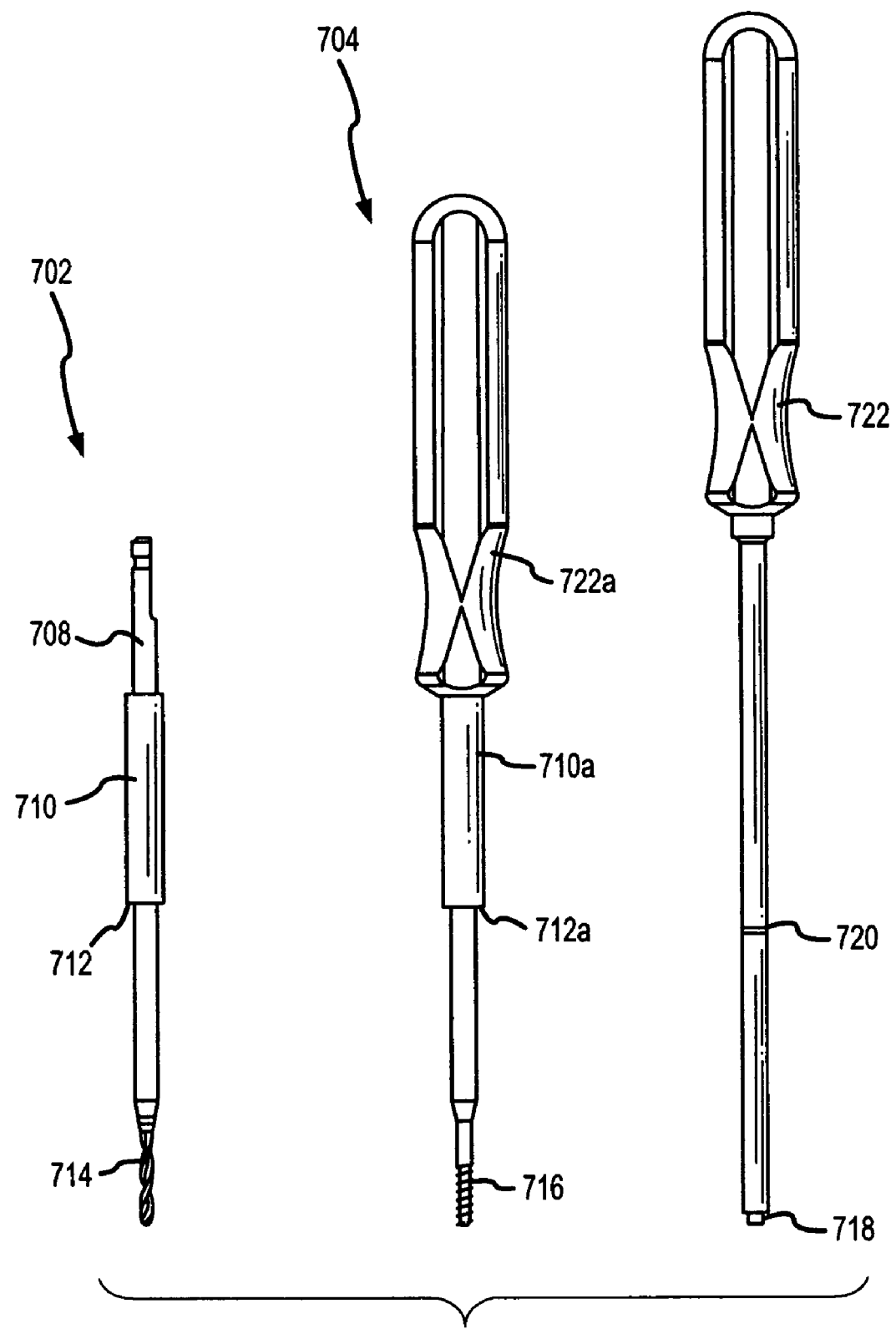
FIG. 7 illustrates embodiments of driver, tap, and drill instruments according to some embodiments of the present invention.

Turning now to FIG. 7, embodiments of various medical instruments that may be used with embodiments of the present invention are provided. A drill 702, a tap 704, and a driver 706 may be used through instrument guide tube 110. Drill 702 may include an interface end 708 to be secured into a manual drill handle 722 or a chuck of a motorized drill drive. Tap 704 and driver 706 include handles 722, 722a. Depth stop collars 710, 710a prevent drilling or tapping too deeply into the bone by permitting drill 702 or tap 704 to be inserted into instrument guide tube 110 only until bottom end 712, 712a of depth stop collar 710, 710a contacts depth stop collar 112 of instrument guide tube 110. Drill 702 includes a drill tip 714; tap 704 includes a tap tip 716; and driver 706 includes a driver tip 718. Driver 706 may be a hex head screw driver. According to some embodiments of the present invention, driver 706 includes a depth stop line 720 to serve as a guide and/or to alert a user that a screw has been driven to a recommended depth through an instrument guide tube 110 and into a bone hole when depth stop line 720 is approximately level with the top of depth stop collar 112 of instrument guide tube 110. The screw may be driven to a recommended depth or until the screw is properly seated. According to some embodiments of the present invention, depth stop line 720 may be used as a guide, such as, for example, a visual guide, to indicate that a screw may have been driven to a certain depth.

Once instrument guide device 100 has been positioned onto cervical plate 200, instrument guide device 100 may be tilted to vary the screw placement angle. Instrument guide device 100 is in a neutral position 806 when alignment stand 106 is vertical with respect to cervical plate 200, as illustrated by the side perspective view of FIG. 8. Instrument guide device 100 may be tilted in one direction to a cephalad position 804, or in the opposite direction to a caudad position 808, as illustrated by arrows 802. When instrument guide device 100 has been tilted a certain angle into the cephalad position 804, or a certain angle into the caudad position 808, angle-limiting post 116 abuts an inner surface of hex hole 206 of locking cap 204 (or other receptacle, as discussed above) to prevent further tilting of instrument guide device 100. In this way, angle-limiting post 116 of alignment stand 106 may be configured to allow a recommended range of tilting angles, such as, for example, twelve degrees in the caudad position 808 to twelve degrees in the cephalad position 804. Allowing a user to select a precise screw placement angle, such as a cephalad angle, a neutral angle, or a caudad angle, from a range of tilt angles may permit screw placement to be customized for a particular patient's anatomy or a particular surgical procedure. In some cases, a slightly cephalad position 804 may be preferred for screw placement.

Figure 9:
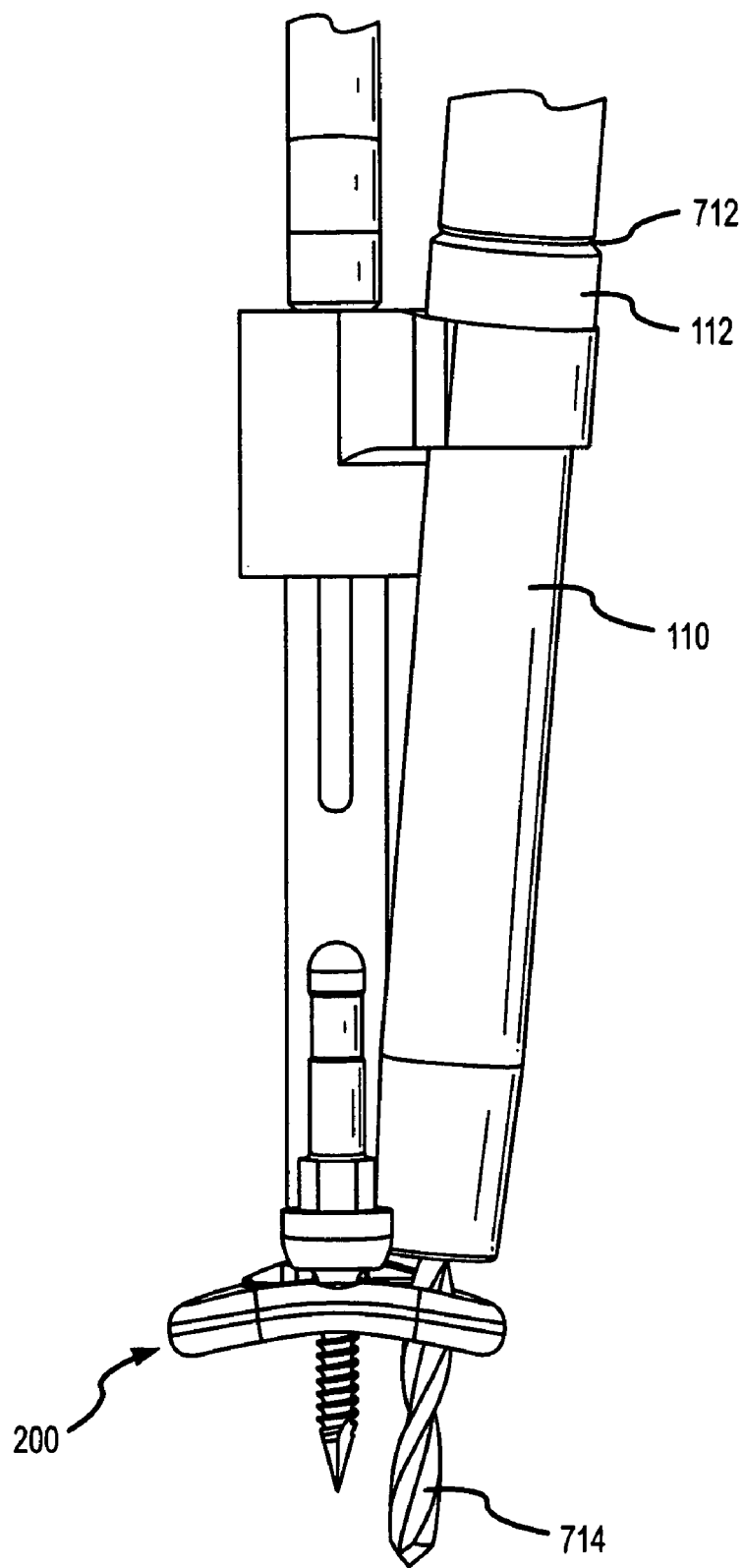
FIG. 9 illustrates a front perspective view of an embodiment of the instrument guide device of FIG. 1 and a cervical plate, in which a drill is passing through the single instrument guide tube according to various embodiments of the present invention.

When a desired screw placement angle has been selected, drill bit 714 is inserted into instrument guide tube 110, as illustrated in FIG. 9. Drill bit 714 is advanced, for example, in a clockwise rotational motion until the bottom 712 of depth stop collar 710 contacts the top of depth stop collar 112 on instrument guide tube 110. This will cause a hole to be drilled into the bone under cervical plate 200; drill bit 714 may also be rotated in a clockwise rotation when removed from the bone hole and instrument guide tube 110, for example. As one skilled in the art will appreciate based on the disclosure provided herein, the depth of the bone hole drilled corresponds to the placement of depth stop collar 112 on instrument guide tube 110 and depth stop collar 712 on drill 702. According to some embodiments of the present invention, a bone hole is drilled approximately twelve millimeters deep before depth stop collar 712 contacts depth stop collar 112.

Figure 10:
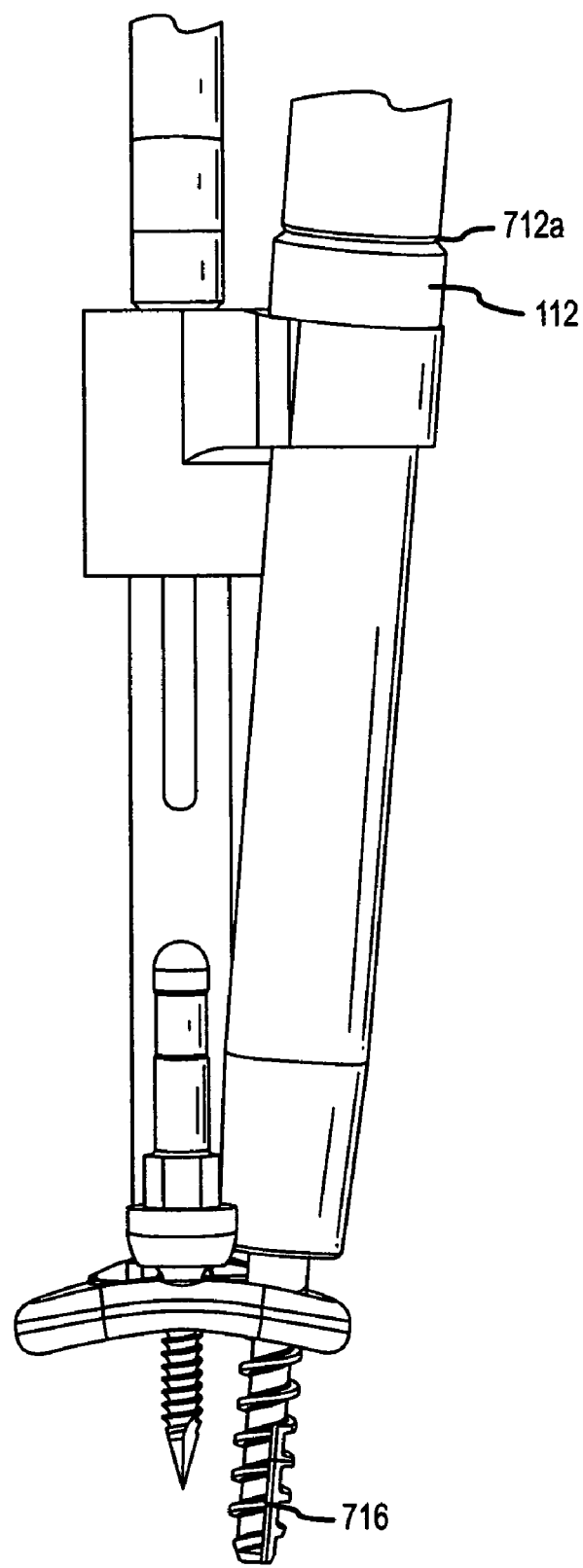
FIG. 10 illustrates a front perspective view of an embodiment of the instrument guide device of FIG. 1 and a cervical plate, in which a tapping tool is passing through the single instrument guide tube according to various embodiments of the present invention.

Once a bone hole has been drilled, tap bit 716 may be inserted into instrument guide tube 110 and into the previously drilled bone hole, as illustrated in FIG. 10. Tap 704 may be advanced, for example, in a clockwise rotational motion until the bottom 712a of depth stop collar 710a contacts the top of depth stop collar 112 on instrument guide tube 110. Once such contact is obtained, the bone hole has been tapped and tap 704 may be rotated, for example, counter-clockwise, until it is free of the bone hole, and removed from instrument guide tube 110. According to some embodiments of the present invention, tapping the drilled hole prior to screw placement is an optional step.

Figure 11:
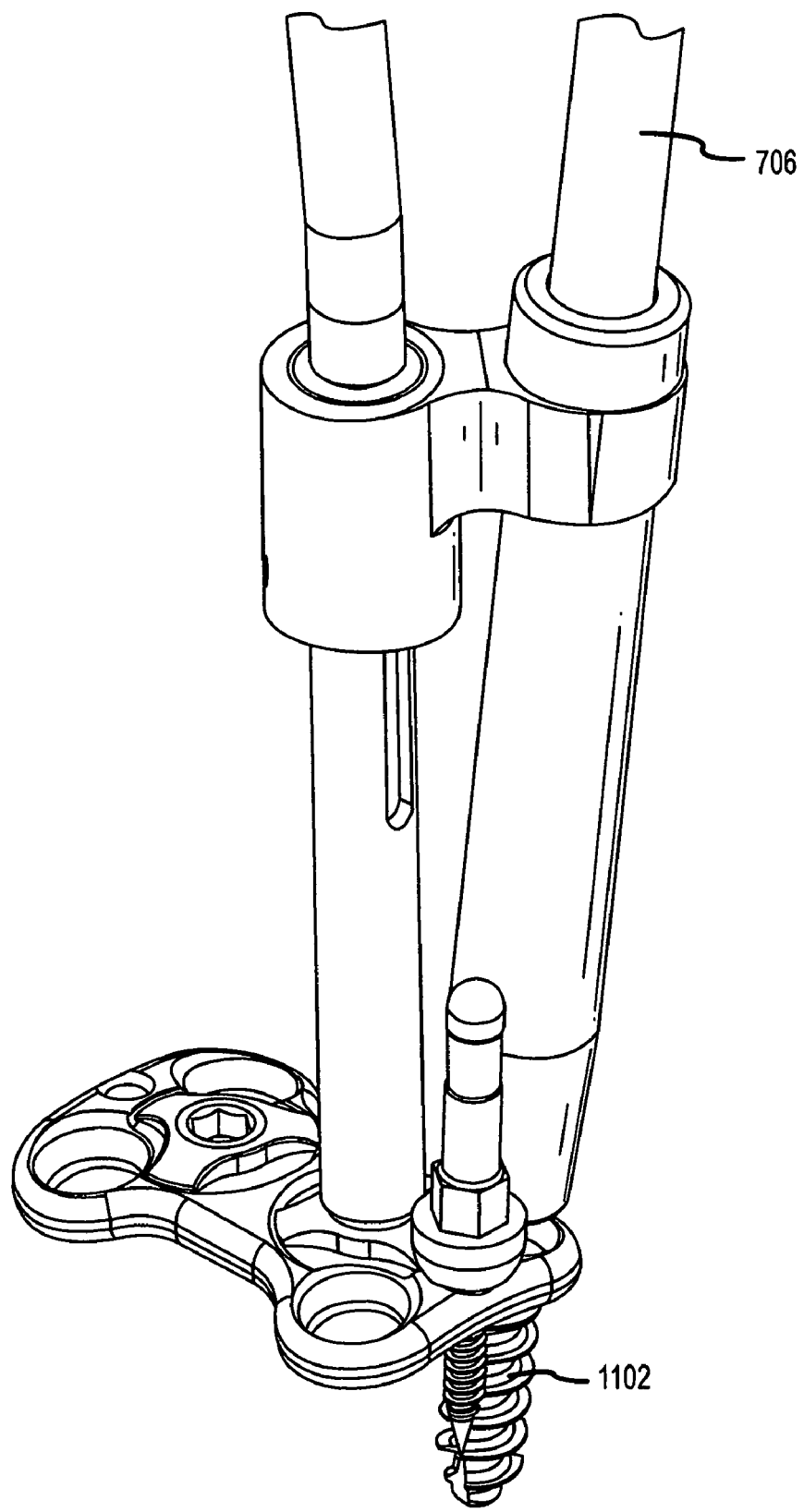
FIG. 11 illustrates a front perspective view of an embodiment of the instrument guide device of FIG. 1 and a cervical plate, in which a fixed-type screw is passing through the single instrument guide tube according to various embodiments of the present invention.
Figure 12:
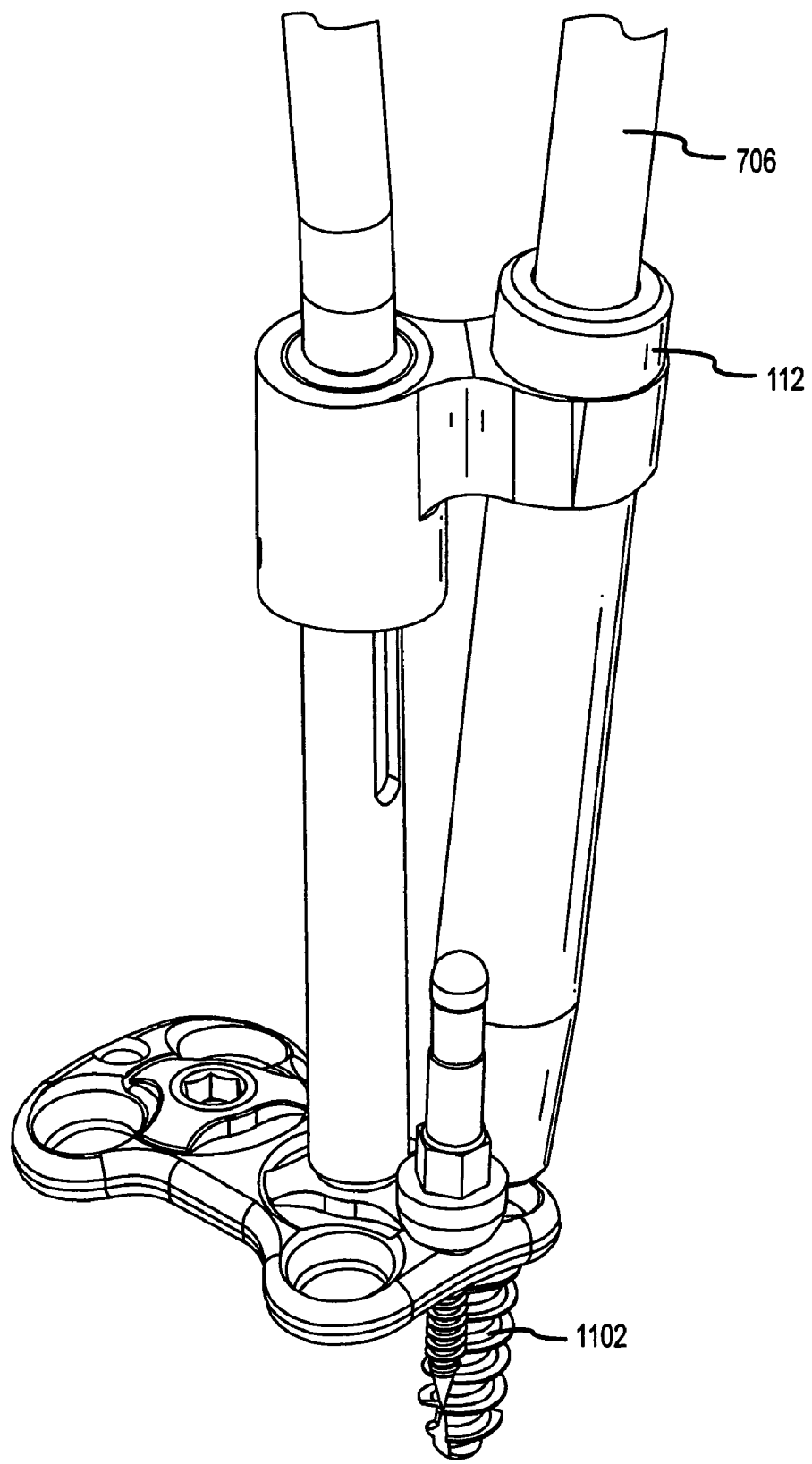
FIG. 12 illustrates a front perspective view of an embodiment of the instrument guide device of FIG. 1 and a cervical plate, in which a variable-type screw is passing through the single instrument guide tube according to various embodiments of the present invention.

When a bone hole has been drilled and tapped, a correct type of screw is selected. The screw type may be fixed or variable. A fixed-type screw may be configured for optimal effectiveness at a certain predetermined screw placement angle; a variable-type screw may be configured for effectiveness at various possible placement angles. Therefore, use of a fixed-type screw may require placement, tilting, and/or angling of instrument guide device 100 corresponding to the certain predetermined screw placement angle. Next, driver tip 718 may be inserted into a socket of the selected screw using downward pressure to secure the screw to driver tip 718. The screw may be a hex-head screw, and driver tip 718 may be a hex driver tip 718. Driver 706 and the screw are positioned in instrument guide tube 110, and the screw tip is inserted into the previously drilled and/or tapped bone hole. Driver 706 is rotated, for example, clockwise to advance the screw until it is firmly seated. According to some embodiments of the present invention, the entire screw may be inserted into and through instrument guide tube 110, through bone screw receiving hole 202, and into the bone hole. FIG. 11 depicts a fixed-type bone screw 1102 and driver 706 inserted through instrument guide tube 110, and FIG. 12 depicts a variable-type bone screw 1202 and driver 706 inserted through instrument guide tube 110. In some cases, final adjustments may be necessary once fixation pin 402 is removed from cervical plate 200. According to some embodiments of the present invention, depth stop line 720 becomes approximately level with the top of depth stop collar 112 of instrument guide tube 110 to indicate that the screw is nearly seated.

Figure 36A:
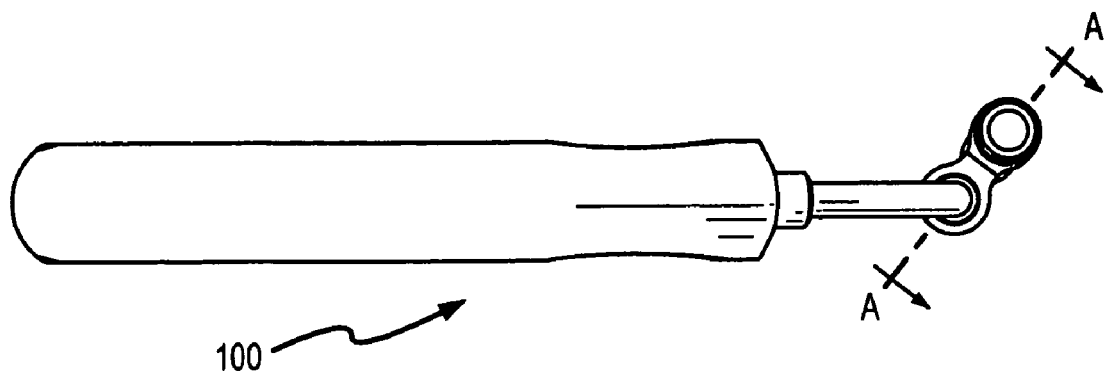
FIG. 36A illustrates a top view of an instrument guide device according to some embodiments of the present invention.
Figure 36B:
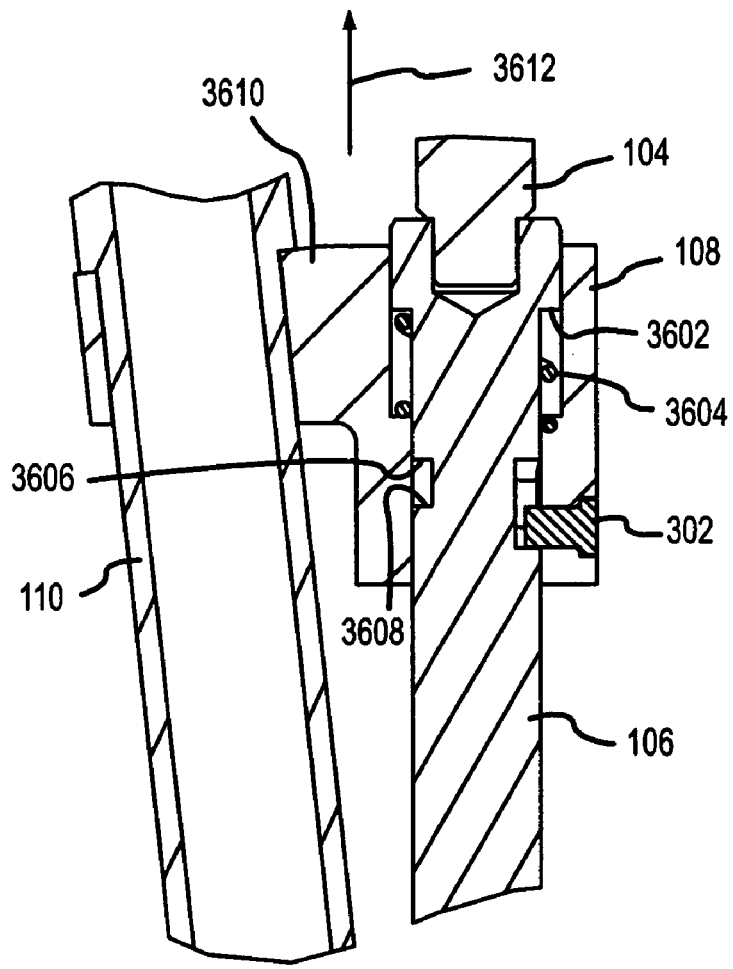
FIG. 36B illustrates a partial cut-away, cross-sectional view of the instrument guide device of FIG. 36A taken along line A-A of FIG. 36A.

Once a first bone screw has been placed through cervical plate 200, instrument guide tube 110 of instrument guide device 100 may be swiveled to a second configuration to permit placement of the next bone screw. FIG. 36A illustrates a top view of instrument guide device 100, and FIG. 36B illustrates a partial cut-away, cross-sectional view of instrument guide device 100 taken along line A-A of FIG. 36A. FIG. 36B also illustrates the operation of one embodiment of rotational coupling 108. In the illustrated embodiment, rotational coupling 108 surrounds the top end of alignment stand 106, and instrument guide tube 110 attaches to rotational coupling 108 via brace portion 3610. Rotational coupling 108 includes an alignment pin 302 which protrudes between an upper lip 3606 and a lower lip 3608 of alignment stand 106; alignment pin 302 prevents disengagement of rotational coupling 108 from alignment stand 106 while permitting rotational coupling 108 to rotate with respect to alignment stand 106. Alignment pin 302 is also operable to halt rotation of rotational coupling 108 while alignment pin 302 is engaged with or seated in one or more alignment slots (discussed in more detail below with reference to FIG. 37A) formed in the lower lip 3608. FIG. 36B depicts alignment pin 302 seated in an alignment slot. In a normal operating position, in which alignment pin 302 is seated in an alignment slot, alignment pin 302 is held within the alignment slot by a spring 3604. Spring 3604 may be coiled around alignment stand 106 and rest in compression between an inner edge of brace portion 3610 and an inner edge 3602 of rotational coupling 108. To disengage alignment pin 302 from the alignment slot, spring 3604 may be further compressed by pulling rotational coupling 108 upward in the direction indicated by arrow 3612. The rotational coupling 108 and instrument guide tube 110 assembly may then be rotated with respect to alignment stand 106 until alignment pin 302 protrudes over another alignment slot. When rotational coupling 108 is released, spring 3604 will expand to hold alignment pin 302 in the other alignment slot.

Figures 37A, 37B, 37C, 37D:
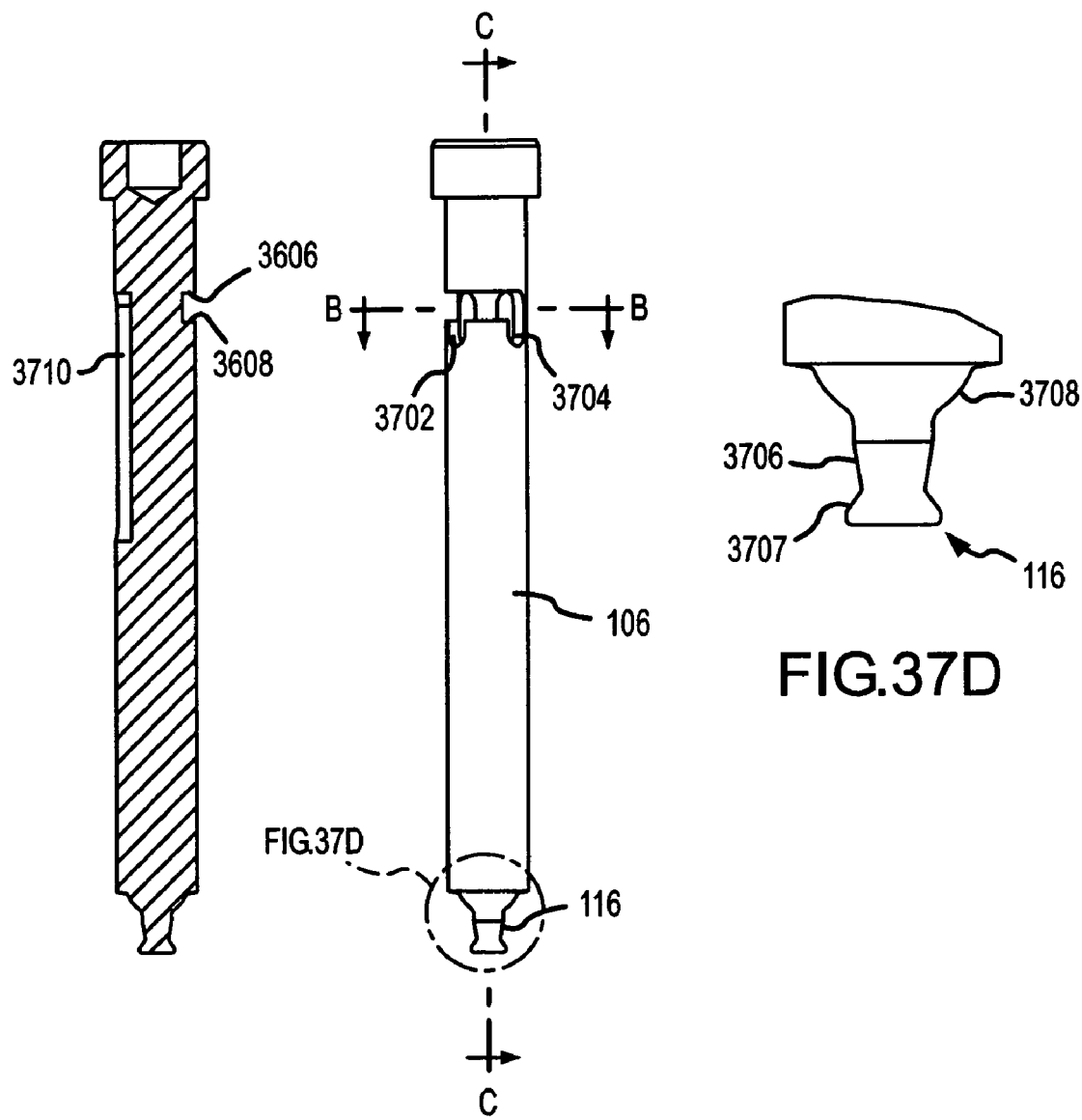
FIG. 37A illustrates a front perspective view of an alignment stand for an instrument guide device having a swiveling single instrument guide tube according to some embodiments of the present invention.
FIG. 37B illustrates a cross-sectional view of the alignment stand of FIG. 37A taken along line B-B of FIG. 37A.
FIG. 37C illustrates a cross-sectional view of the alignment stand of FIG. 37A taken along line C-C of FIG. 37A.
FIG. 37D illustrates an enlarged front perspective view of an angle-limiting post taken from within circle FIG. 37D of FIG. 37A.

FIG. 37A illustrates a front perspective view of an alignment stand 106 for an instrument guide device 100 having a swiveling single instrument guide tube according to some embodiments of the present invention. FIG. 37B illustrates a cross-sectional view of the alignment stand taken along line B-B of FIG. 37A. FIG. 37C illustrates a cross-sectional view of the alignment stand taken along line C-C of FIG. 37A. FIG. 37D illustrates an enlarged front perspective view of an angle-limiting post 116 taken from within circle FIG. 37D of FIG. 37A. In this particular embodiment, alignment post 116 includes an upper lip 3606 and a lower lip 3608. Alignment slots 3702, 3704 are formed within lower lip 3608. According to some embodiments of the present invention, alignment slots 3702 and 3704 are separated on lower lip 3608 by an angle of about one hundred three degrees. Alignment stand 106 may further include a third slot 3710 formed, for example, within lower lip 3608. Slot 3710 may extend further along alignment stand 106 and be deeper than alignment slots 3702, 3704. Slot 3710 may permit rotational coupling 108 to be rotated to a third position and slid away from slots 3702 and 3704; in this fashion, slot 3710 may permit rotational coupling 108 to be slid away from slots 3702 and 3704 to expose the area of alignment stand 106 around slots 3702 and 3704, to permit cleaning of slots 3702 and 3704 and the surrounding area.

Angle-limiting post 116 of alignment stand 106 may be configured to allow a recommended range of tilting angles, as depicted in FIG. 37D. Alignment post 116 may comprise a ball portion 3708, a neck portion 3706, and a flare portion 3707. Neck portion 3706 and flare portion 3707 may be configured to fit within hex hole 206 of locking cap portion 204 (or other receptacle, as discussed above) of cervical plate 200. Ball portion 3708 may be configured to contact a perimeter of hex hole 206 when neck portion 3706 and flare portion 3707 are inserted into hex hole 206. Ball portion 3708 may facilitate tilting of alignment stand 106 while making physical contact with hex hole 206. According to some embodiments of the present invention, ball portion 3708 acts as a ball, and a perimeter of hex hole 206 acts as a socket, and ball portion 3708 is configured to roll or tilt within hex hole 206. The length of neck portion 3706 may be increased or decreased to fit hex holes 206 of varying depth, to permit ball portion 3708 to ride on top of a hex hole 206 with greater or lesser depth. As alignment post 106 is tilted, flare portion 3707 contacts an inside of hex hole 206 to limit the angle of tilt. Thus, a diameter of flare portion 3707 may be decreased to permit a larger degree of tilt, or a diameter of flare portion 3707 may be increased to permit a smaller degree of tilt. As the diameter of neck portion 3706 and/or flare portion 3707 increases, the range of tilt angle decreases, until a point at which angle limiting post 116 more closely resembles stem 1718 of FIG. 17.

Figure 13A:
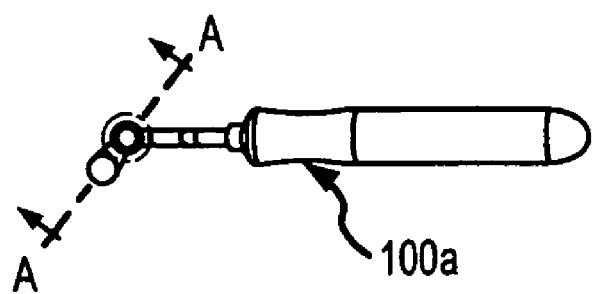
FIG. 13A illustrates a top perspective view of an instrument guide device according to some embodiments of the present invention.
Figure 13B:
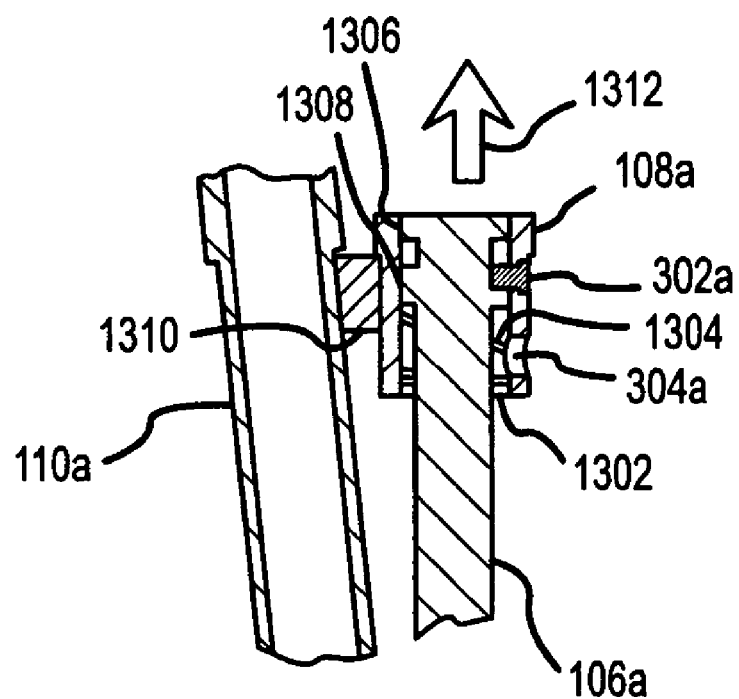
FIG. 13B illustrates a partial cut-away, cross-sectional view of the embodiment of the instrument guide device of FIG. 13A taken along line A-A of FIG. 13A.

FIGS. 13A through 14C depict alternative embodiments of a rotational coupling 108a and alignment post 106a of an instrument guide device 100a according to various embodiments of the present invention. FIG. 13A illustrates a top view of instrument guide device 100a, and FIG. 13B illustrates a partial cut-away, cross-sectional view of instrument guide device 100a taken along line A-A of FIG. 13A. FIG. 13B also illustrates the operation of one embodiment of rotational coupling 108a. In the illustrated embodiment, rotational coupling 108a surrounds the top end of alignment stand 106a, and instrument guide tube 110a attaches to rotational coupling 108a via brace portion 1310a. Rotational coupling 108a includes an alignment pin 302a which protrudes between an upper lip 1306 and a lower lip 1308 of alignment stand 106a; alignment pin 302a prevents disengagement of rotational coupling 108a from alignment stand 106a while permitting rotational coupling 108a to rotate with respect to alignment stand 106a. Alignment pin 302a is also operable to halt rotation of rotational coupling 108a while alignment pin 302a is engaged with or seated in one or more alignment slots (discussed in more detail below with reference to FIG. 14A) formed in the lower lip 1308. FIG. 13B depicts alignment pin 302a seated in an alignment slot. In a normal operating position, in which alignment pin 302a is seated in an alignment slot, alignment pin 302a is held within the alignment slot by a spring 1304. Spring 1304 may be coiled around alignment stand 106a and rest in compression between the bottom side of lower lip 1308 and a bottom collar 1302 of rotational coupling 108a. To disengage alignment pin 302a from the alignment slot, spring 1304 may be further compressed by pulling rotational coupling 108a upward in the direction indicated by arrow 1312. The rotational coupling 108a and instrument guide tube 110a assembly may then be rotated with respect to alignment stand 106a until alignment pin 302a protrudes over another alignment slot. When rotational coupling 108a is released, spring 1304 will expand to hold alignment pin 302 in the other alignment slot.

Figure 14B:
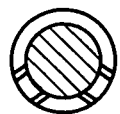
FIG. 14B illustrates a cross-sectional view of the alignment stand of FIG. 14A taken along line B-B of FIG. 14A.
Figure 14C:
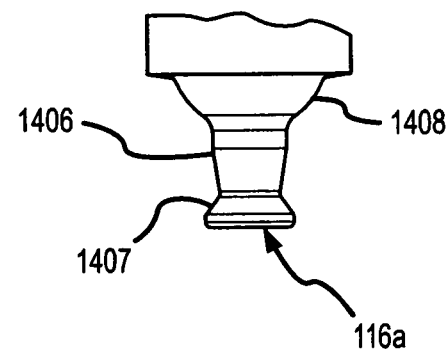
FIG. 14C illustrates an enlarged front perspective view of an angle-limiting post taken from within circle FIG. 14C of FIG. 14A.
Figure 14A:
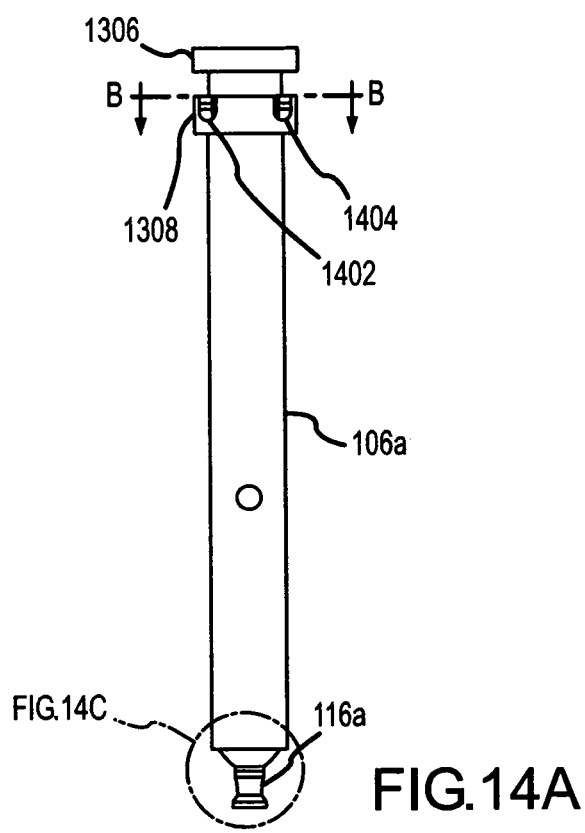
FIG. 14A illustrates a front perspective view of an alignment stand for an embodiment of the instrument guide device of FIGS. 13A and 13B according to some embodiments of the present invention.

FIG. 14A illustrates a front perspective view of an alignment stand 106a for an instrument guide device 100a having a swiveling single instrument guide tube according to some embodiments of the present invention. FIG. 14B illustrates a cross-sectional view of the alignment stand taken along line B-B of FIG. 14A. FIG. 14C illustrates a detailed front perspective view of an angle-limiting post 116a taken from within circle FIG. 14C of FIG. 14A. In this particular embodiment, alignment post 116a includes an upper lip 1306 and a lower lip 1308. Alignment slots 1402, 1404 are formed within lower lip 1308. According to some embodiments of the present invention, alignment slots 1402 and 1404 are separated on lower lip 1308 by an angle of about one hundred three degrees.

Figure 8:
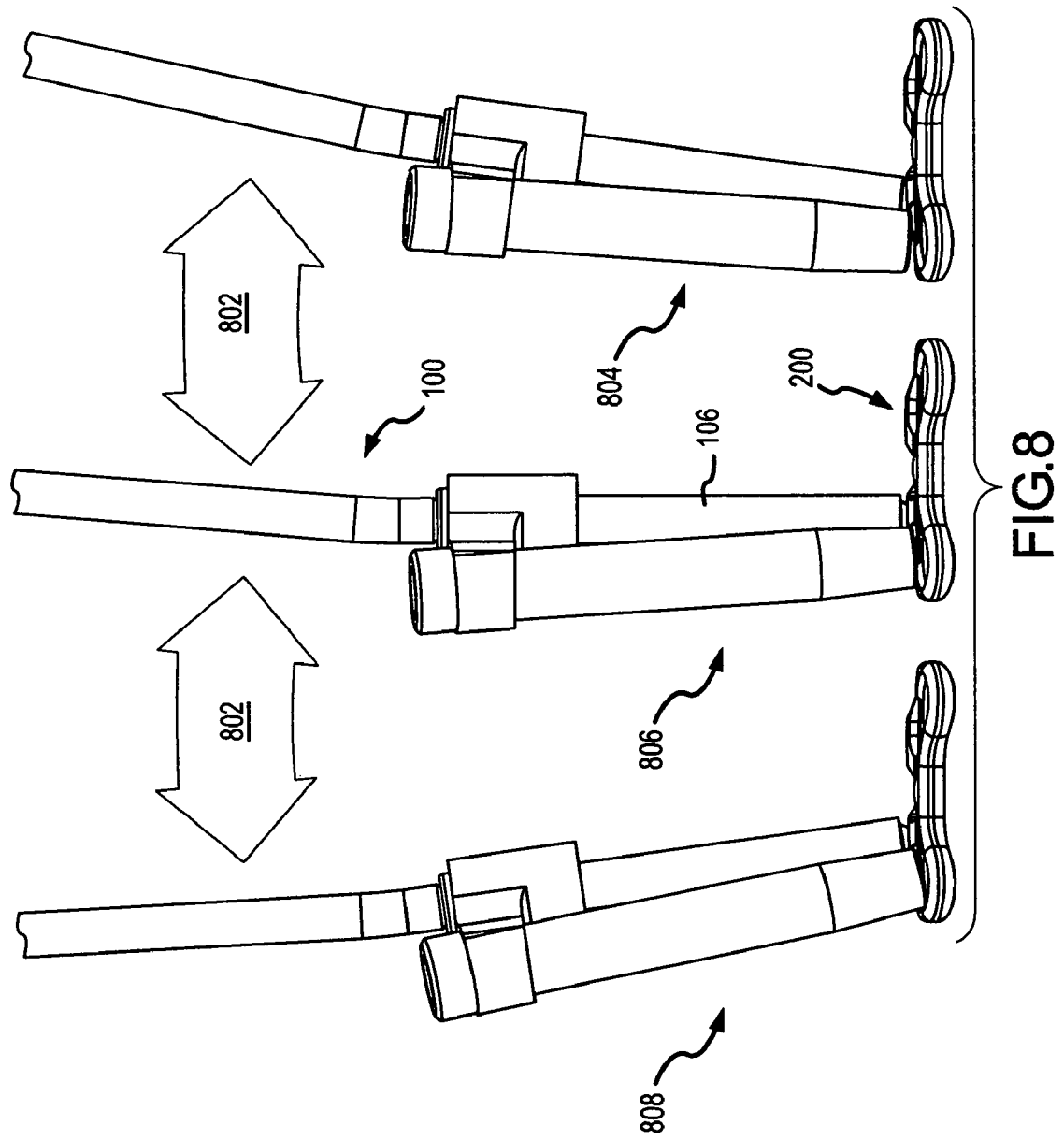
FIG. 8 illustrates side perspective views of embodiments of the instrument guide devices of FIG. 1 tilted at different angles with respect to a cervical plate according to various embodiments of the present invention.

Angle-limiting post 116a of alignment stand 106 may be configured to allow a recommended range of tilting angles, as depicted in FIG. 8. Alignment post 116a may comprise a ball portion 1408, a neck portion 1406, and a flare portion 1407. Neck portion 1406 and flare portion 1407 may be configured to fit within hex hole 206 of locking cap portion 204 (or other receptacle, as discussed above) of cervical plate 200. Ball portion 1408 may be configured to contact a perimeter of hex hole 206 when neck portion 1406 and flare portion 1407 are inserted into hex hole 206. Ball portion 1408 may facilitate tilting of alignment stand 106a while making physical contact with hex hole 206. According to some embodiments of the present invention, ball portion 1408 acts as a ball, and a perimeter of hex hole 206 acts as a socket, and ball portion 1408 is configured to roll or tilt within hex hole 206. The length of neck portion 1406 may be increased or decreased to fit hex holes 206 of varying depth, to permit ball portion 1408 to ride on top of a hex hole 206 with greater or lesser depth. As alignment stand 106 is tilted, flare portion 1407 contacts an inside of hex hole 206 to limit the angle of tilt. Thus, a diameter of flare portion 1407 may be decreased to permit a larger degree of tilt, or a diameter of flare portion 1407 may be increased to permit a smaller degree of tilt. As the diameter of neck portion 1406 and/or flare portion 1407 increases, the range of tilt angle decreases, until a point at which angle limiting post 116a more closely resembles stem 1718 of FIG. 17.

Figure 15:
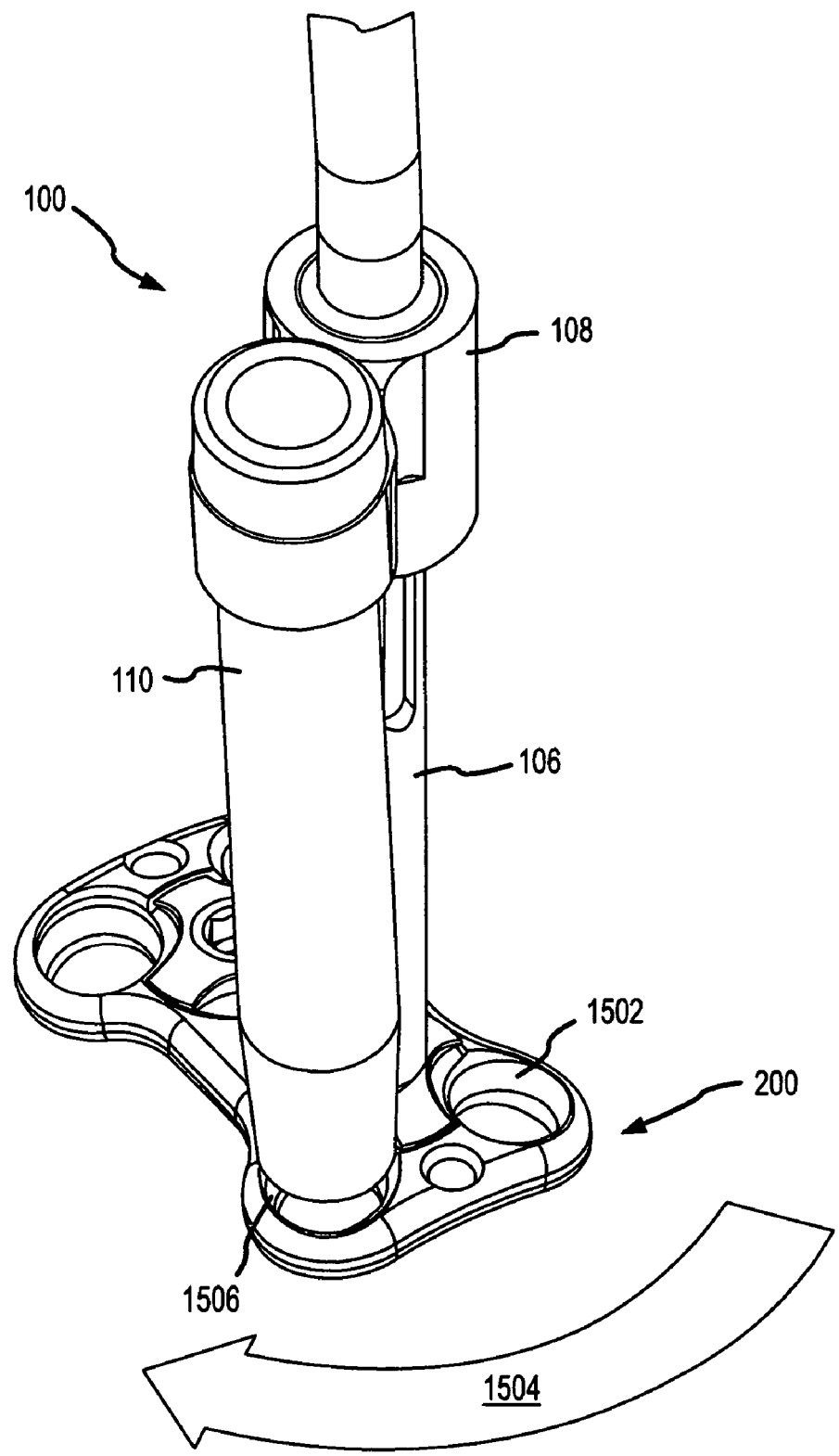
FIG. 15 illustrates a procedure for rotating the single instrument guide tube of an embodiment of the instrument guide device of FIG. 1 according to some embodiments of the present invention.

FIG. 15 illustrates a procedure for rotating a single instrument guide tube 110 of instrument guide device 100 according to some embodiments of the present invention. Instrument guide tube 110 begins in a first position over bone screw receiving hole 1502 and with alignment pin 302 in alignment slot 3704. To rotate instrument guide tube 110, rotational coupling 108 is lifted upward to unseat alignment pin 302, and instrument guide tube 110 is rotated in the direction indicated by arrow 1504. When alignment pin 302 passes over alignment slot 3702 and rotational coupling 108 is released, spring 1304 seats alignment pin 302 in alignment slot 3702, and instrument guide tube 110 is then in position over bone screw receiving hole 1506. According to some embodiments of the present invention, rotational coupling 108 is lifted upward only during initial rotation, after which rotational coupling 108 is released and instrument guide tube 110 rotates freely until a positive stop is reached by alignment pin 302 encountering alignment slot 3702. In some cases, fixation pin 402 is removed from cervical plate 200 to allow instrument guide tube 110 to rotate while alignment stand 106 is seated in hex hole 206 of locking cap 204.

Figure 16:
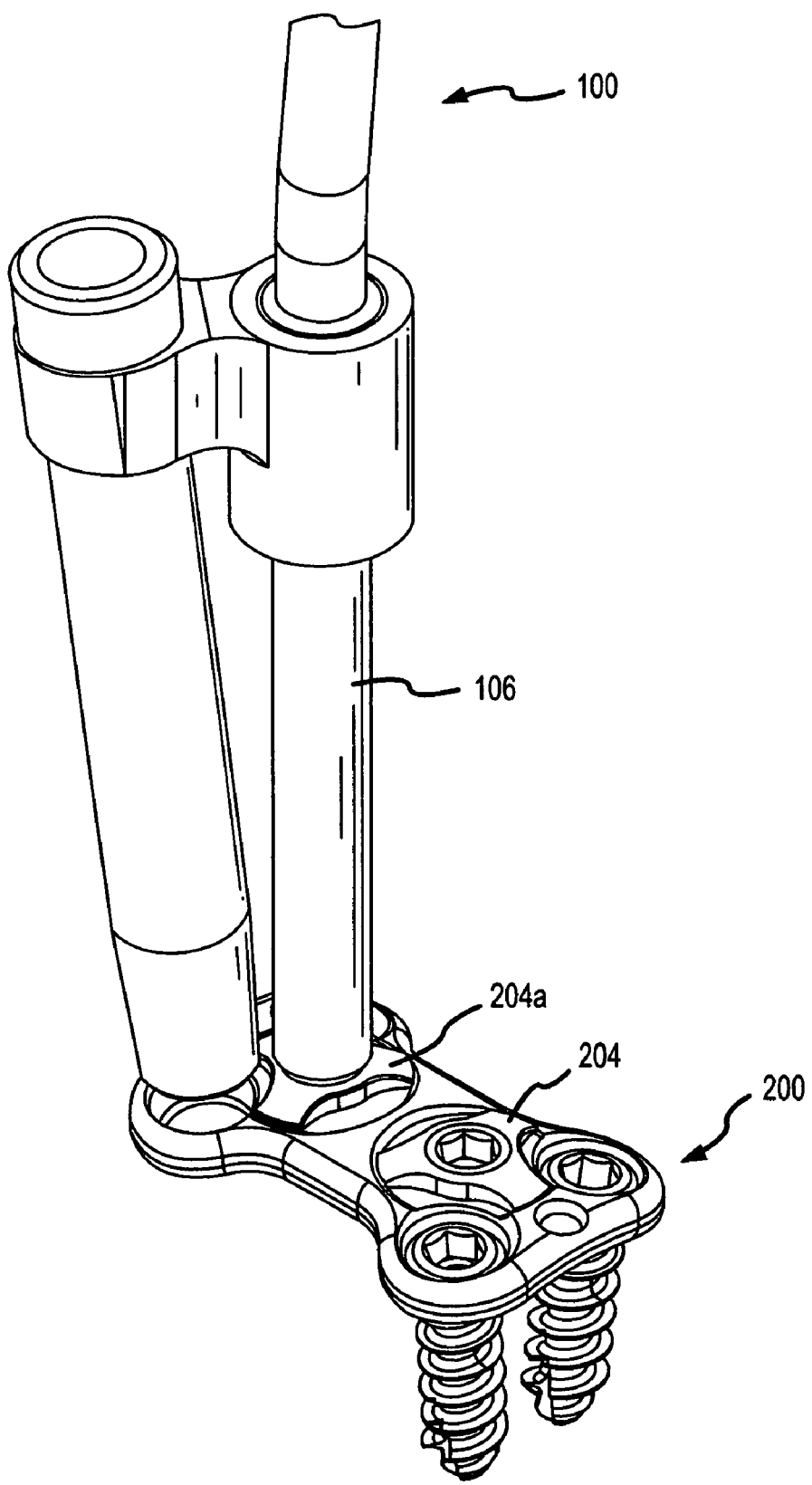
FIG. 16 illustrates a procedure for repositioning an embodiment of the instrument guide device of FIG. 1 on a cervical plate according to some embodiments of the present invention.
Figure 17:
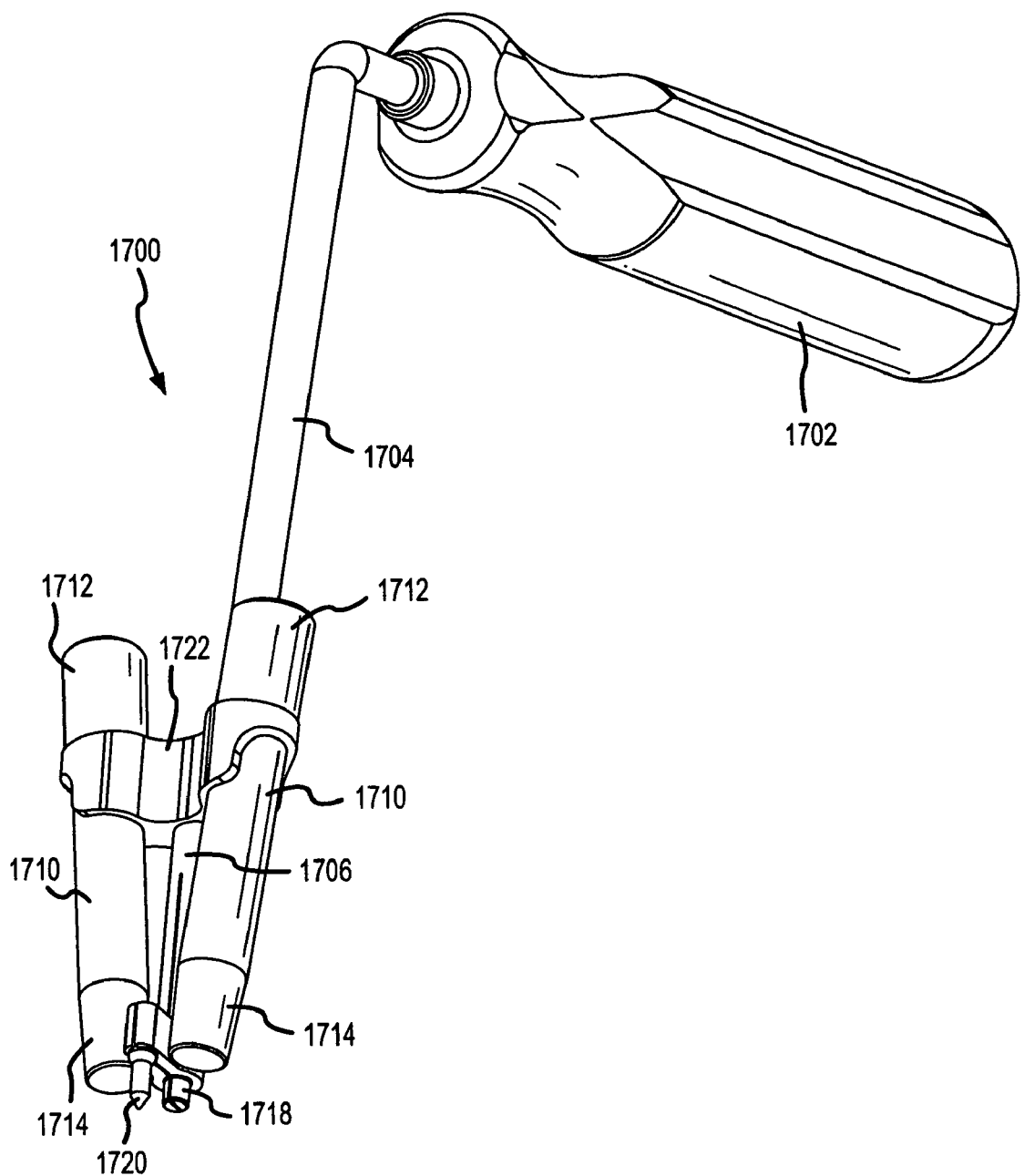
FIG. 17 illustrates an isometric view of an instrument guide device having a fixed double instrument guide tube configuration according to some embodiments of the present invention.

FIG. 16 illustrates a procedure for repositioning instrument guide device 100 on a cervical plate 200 according to some embodiments of the present invention. Once bone screws have been placed through bone screw receiving holes 202 of one side of cervical plate 200, alignment stand 106 of instrument guide device 100 may be lifted from locking cap 204 and inserted into locking cap 204a of cervical plate 200 for placement of bone screws through remaining bone screw receiving holes 202. FIG. 16 illustrates such a procedure for cervical plate 200 through which two fixed-type bone screws 1102 or two variable-type bone screws 1202 have been placed on one side of cervical plate 200.

Figure 18A:
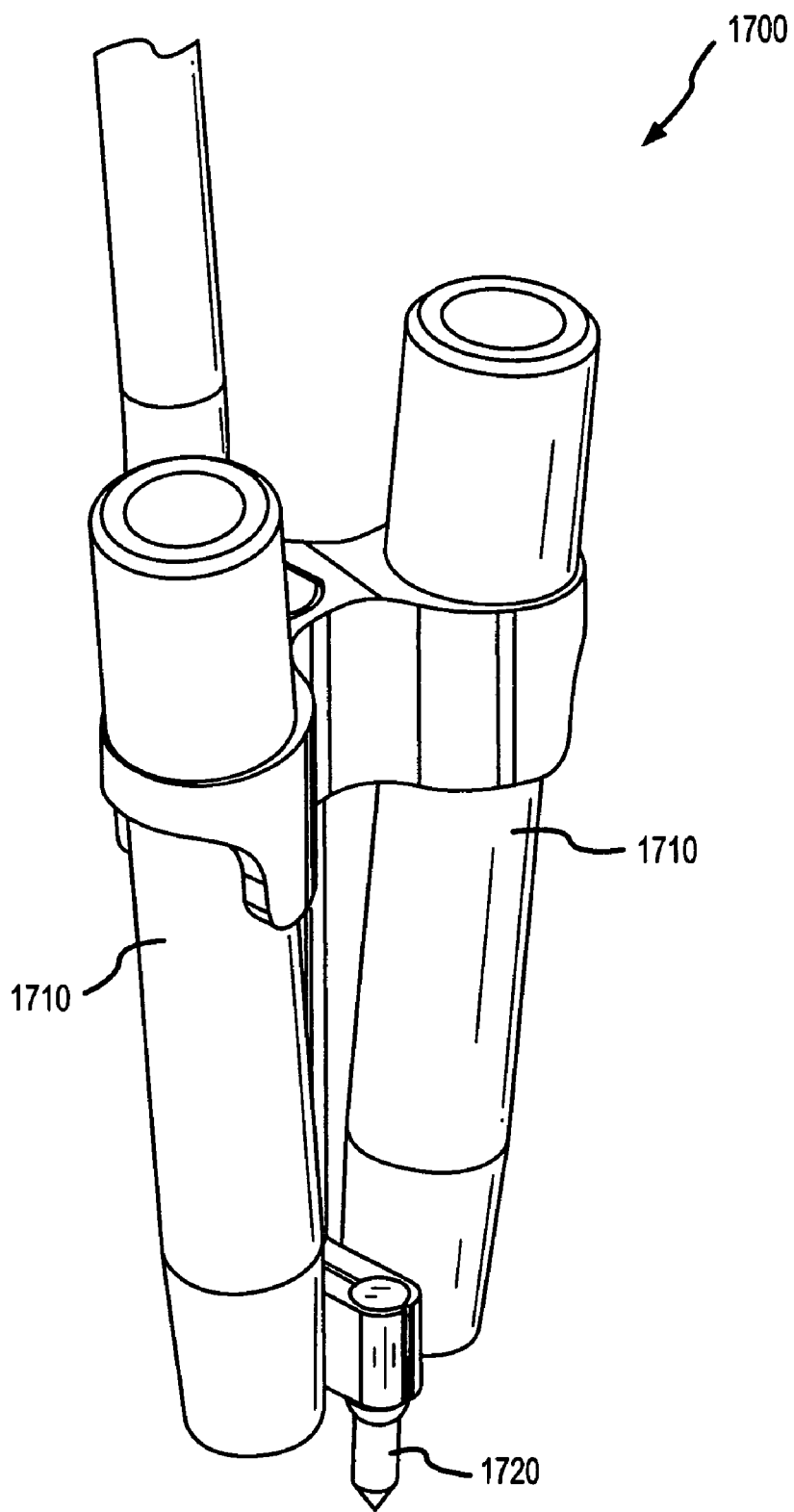
FIG. 18A illustrates a closer view of the device in FIG. 17.
Figure 18B:
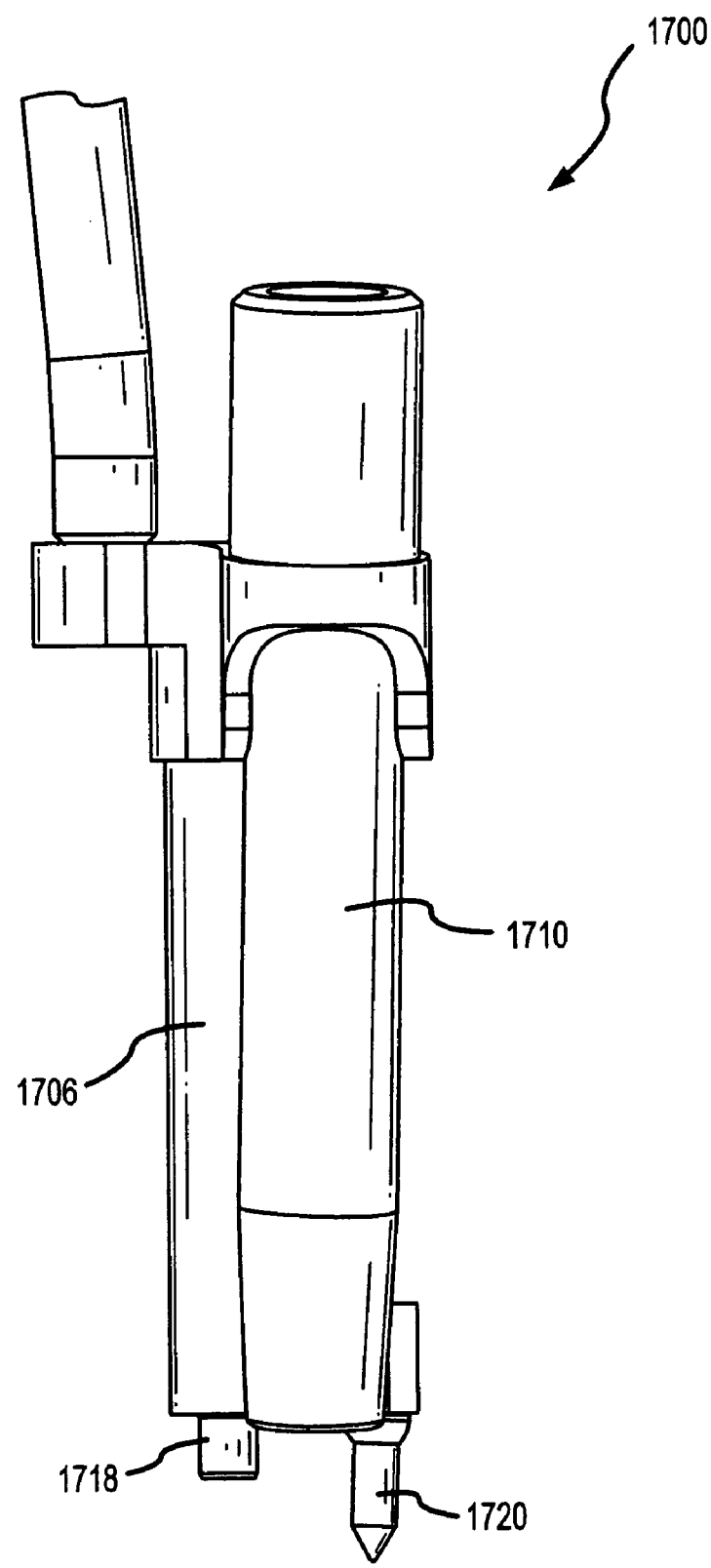
FIG. 18B illustrates a side perspective view of the device in FIG. 17.

Turning now to FIGS. 17, 18A, 18B, and 2, an instrument guide device 1700 having two fixed instrument guide tubes and cervical plate 200 according to some embodiments of the present invention are illustrated. Instrument guide device 1700 includes a handle 1702 and a handle shaft 1704 for holding instrument guide device 1700. According to some embodiments of the present invention, handle 1702 may be removable from handle shaft 1704. A brace portion 1722 is attached to handle shaft 1704, and an alignment stand 1706 is attached to brace portion 1722 and configured to interface with a receptacle in cervical plate 200 via stem 1718. For example, in some embodiments, alignment stand 1706 can interface with locking cap 204 in cervical plate 200. A bone pin 1720 is attached to alignment stand 1706 to hold cervical plate 200 to underlying bone until one or more bone screws have been placed through bone screw receiving holes 202. Instrument guide tubes 1710 having lumens therein are affixed to brace portion 1722. Instrument guide tube 1710 includes a depth stop collar 1712 at a top end for contacting and stopping instruments that have been inserted a predetermined depth into instrument guide tube 1710. Instrument guide tube 1710 also includes a tapered end 1714. FIG. 18A illustrates an isometric view, and FIG. 18B illustrates a side perspective view, of instrument guide device 1700 according to some embodiments of the present invention.

Figure 19:
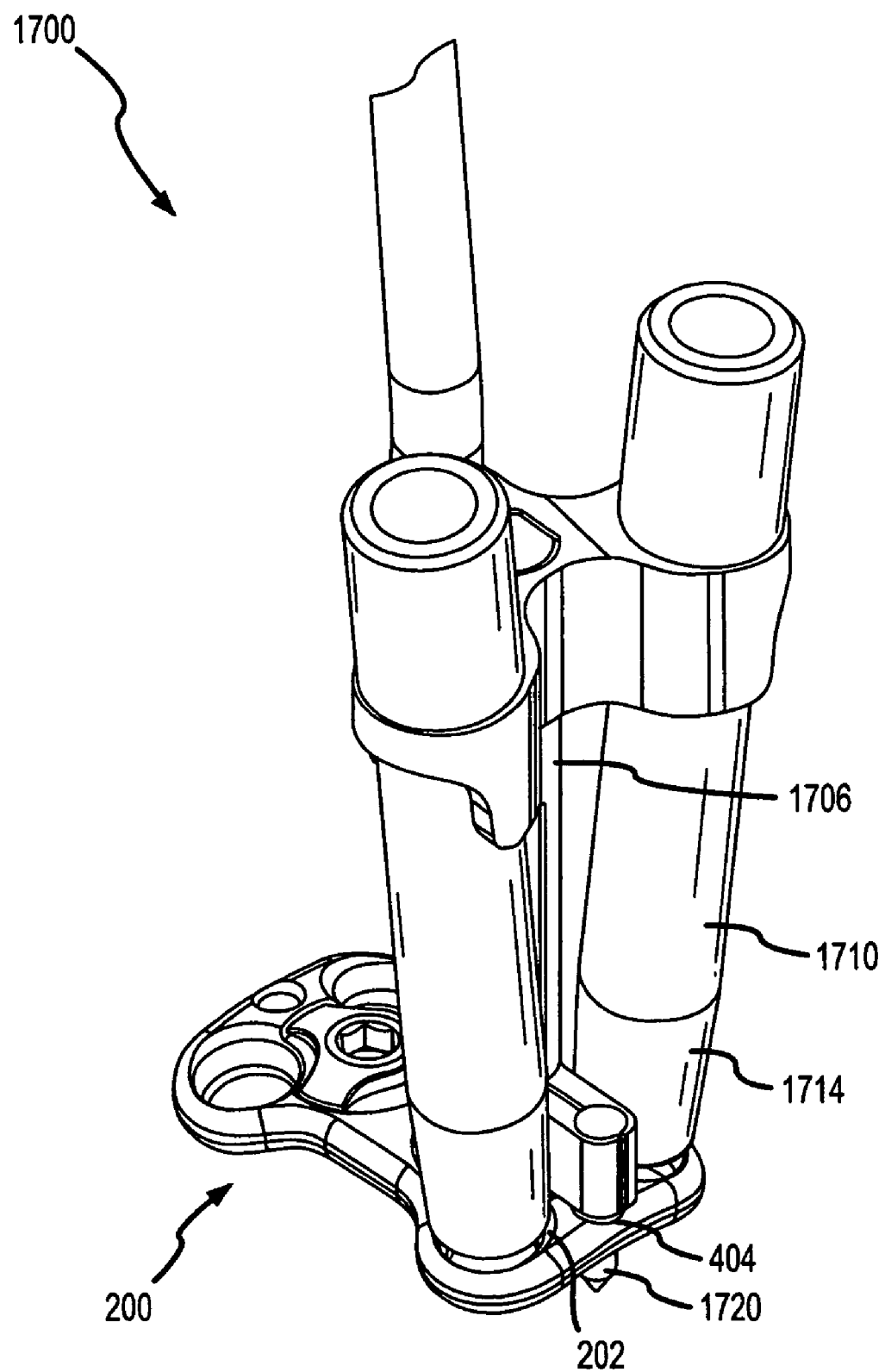
FIG. 19 illustrates an isometric view of an embodiment of the instrument guide device of FIG. 17 placed onto an embodiment of a cervical plate according to some embodiments of the present invention.
Figure 20:
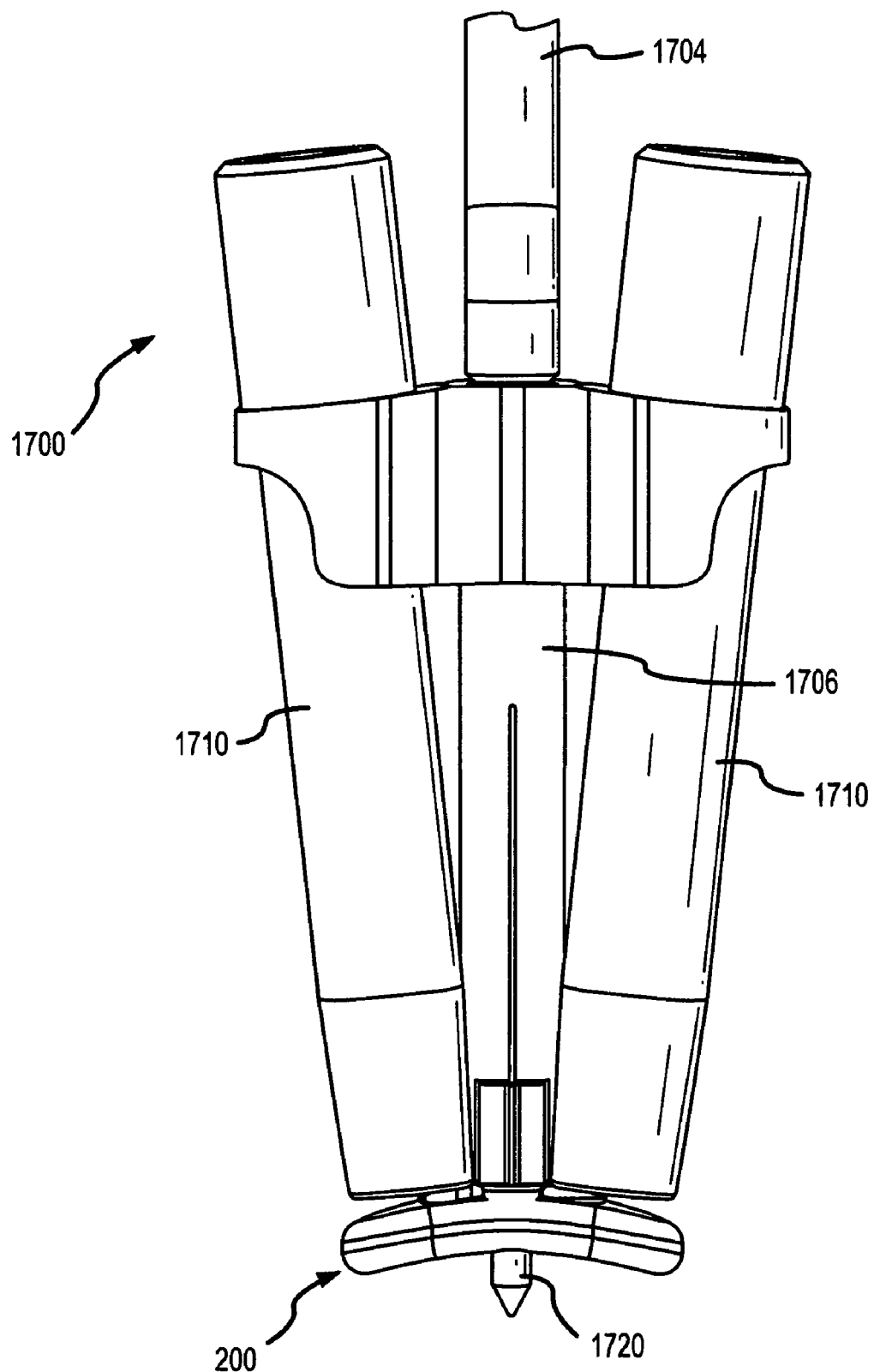
FIG. 20 illustrates a front perspective view of the configuration of FIG. 19.
Figure 21:
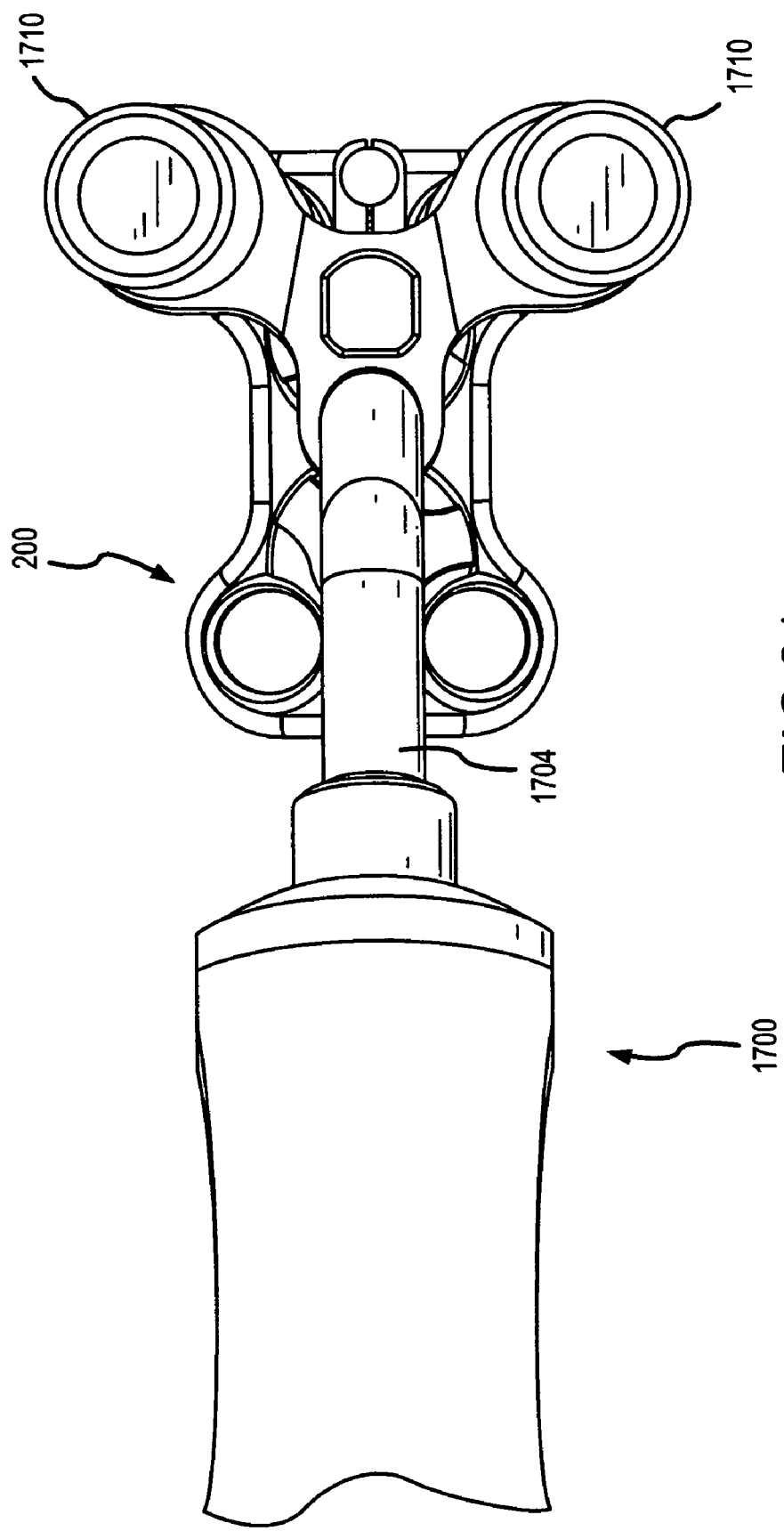
FIG. 21 illustrates a top perspective view of the configuration of FIGS. 19 and 20.

FIG. 19 illustrates an isometric view of instrument guide device 1700 placed onto an embodiment of a cervical plate 200 according to some embodiments of the present invention. In a common scenario, cervical plate 200 is selected and positioned on the midline of the vertebral bodies. Stem 1718 of alignment stand 1706 is inserted into hex hole 206 of locking cap 204 (or other receptacle as described above) on cervical plate 200. Stem 1718 may be a cylindrical head, and is operable to mount within hex hole 206 so as to permit little or no tilting of alignment post 1706, and thus instrument guide device 1700, with respect to locking cap 204. According to other embodiments, stem 1718 may be hex-shaped or otherwise shaped to interface with hex hole 206 and/or locking cap 204. Handle shaft 1704 is then aligned over the midline of cervical plate 200, as depicted in FIGS. 20 and 21, to avoid drilling or placing screws too far medially or laterally. When alignment stand 1706 has been inserted into locking cap portion 204 (or other receptacle, as described above), each instrument guide tube 1710 is positioned over a bone screw receiving hole 202 and an axial center line of each instrument guide tube 1710 passes through a bone screw receiving hole 202, as depicted, for example, in FIGS. 19-21. When stem 1718 of alignment stand 1706 has been inserted into locking cap portion 204 (or other receptacle, as described above), bone pin 1720 passes through fixation hole 404, and may serve to hold cervical plate 200 in position as screws are placed through bone screw receiving holes 202. Bone pin 1720 may include a pointed end for penetrating the underlying bone. According to some embodiments of the present invention, bone pin 1720 and/or instrument guide device 1700 may be tapped with a hand and/or mallet to set bone pin 1720 into the underlying bone. Tapered end 1714 of instrument guide tube 1710 may hover over bone screw receiving hole 202. Alternatively, tapered end 1714 of instrument guide tube 1710 may fit on or within bone screw receiving hole 202 when stem 1718 is inserted into hex hole 206. Alternatively, end 1714 may be non-tapered and/or flared.

Figure 22:
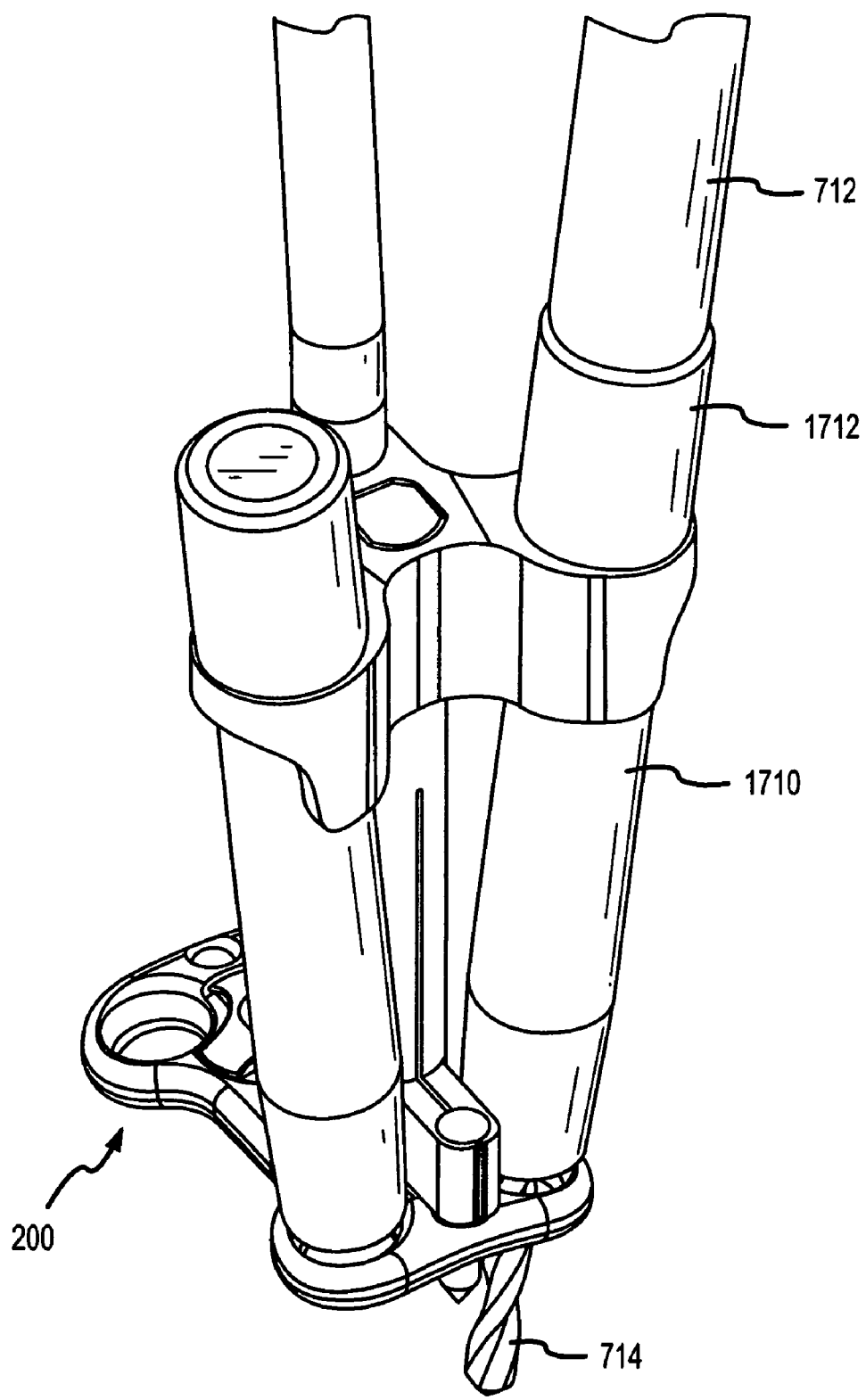
FIG. 22 illustrates an isometric view of an embodiment of the instrument guide device of FIG. 17 placed onto an embodiment of a cervical plate, with a drill inserted through one of the instrument guide tubes according to some embodiments of the present invention.

When instrument guide device 1700 and cervical plate 200 have been positioned over the midline of the vertebral bodies, drill bit 714 is inserted into instrument guide tube 1710, as illustrated in FIG. 22. Drill bit 714 is advanced, for example, in a clockwise rotational motion until the bottom 712 of depth stop collar 710 contacts the top of depth stop collar 1712 on instrument guide tube 1710. This will cause a hole to be drilled into the bone under cervical plate 200; drill bit 714 may also be rotated, for example, in a clockwise rotation when removed from the bone hole and instrument guide tube 1710. As one skilled in the art will appreciate based on the disclosure provided herein, the depth of the bone hole drilled corresponds to the placement of depth stop collar 1712 on instrument guide tube 1710 and depth stop collar 712 on drill 702. According to some embodiments of the present invention, a bone hole can be drilled approximately twelve millimeters deep before depth stop collar 712 contacts depth stop collar 1712.

Figure 23:
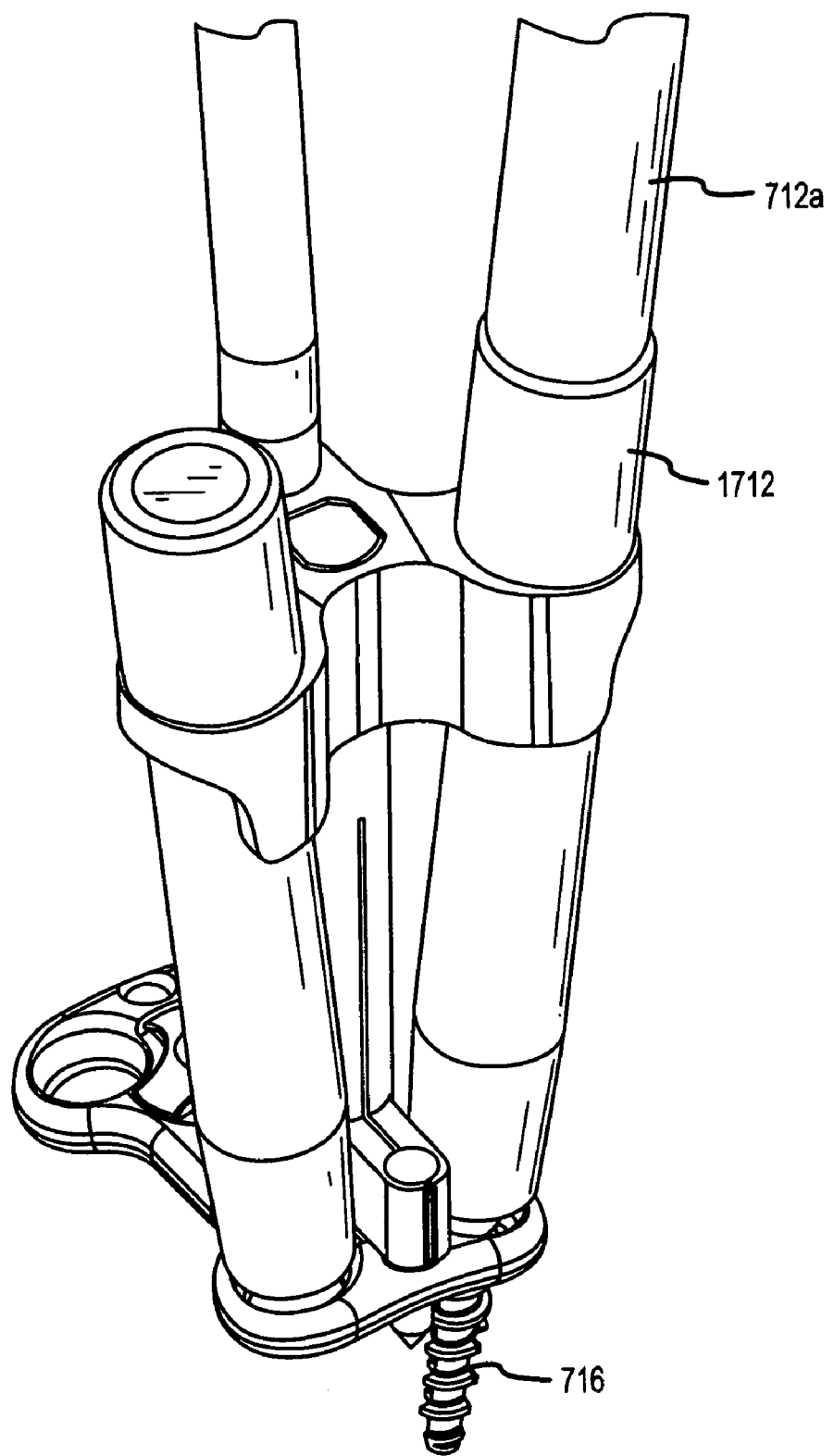
FIG. 23 illustrates an isometric view of an embodiment of the instrument guide device of FIG. 17 placed onto an embodiment of a cervical plate, with a tapping tool inserted through one of the instrument guide tubes according to some embodiments of the present invention.

Once a bone hole has been drilled, tap bit 716 may be inserted into instrument guide tube 1710 and into the previously drilled bone hole, as illustrated in FIG. 23. Tap 704 may be advanced, for example, in a clockwise rotational motion until the bottom 712a of depth stop collar 710a contacts the top of depth stop collar 1712 on instrument guide tube 1710. Once such contact is obtained, the bone hole has been tapped and tap 704 may be rotated, for example, counter-clockwise, until it is free of the bone hole, and removed from instrument guide tube 1710. According to some embodiments of the present invention, tapping the drilled hole prior to screw placement can be an optional step.

Figure 24:
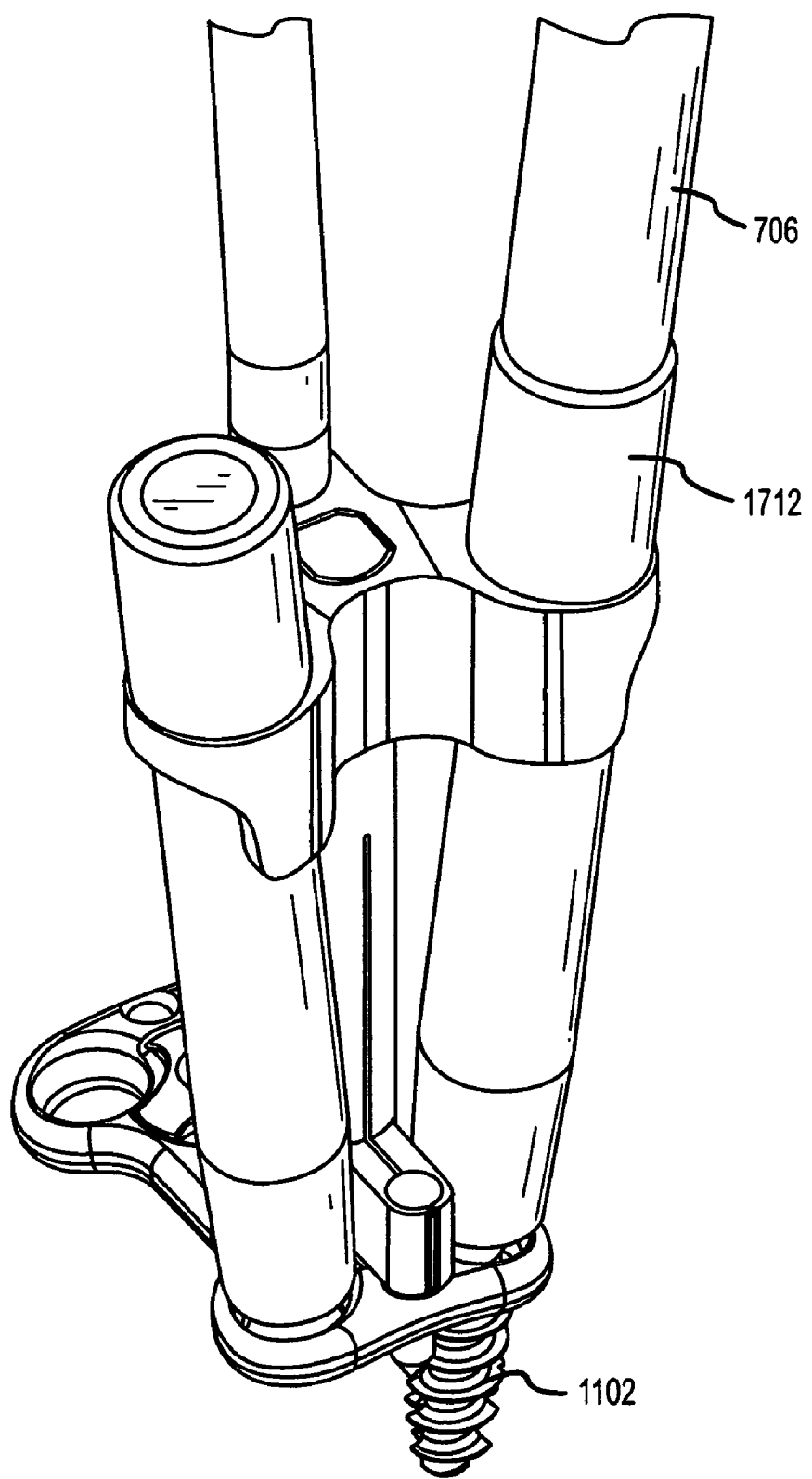
FIG. 24 illustrates an isometric view of an embodiment of the instrument guide device of FIG. 17 placed onto an embodiment of a cervical plate, with a fixed-type screw and screw driver inserted through one of the instrument guide tubes according to some embodiments of the present invention.

When a bone hole has been drilled and tapped, a correct type of screw is selected. The screw type may be fixed or variable, for example. A fixed-type screw may be selected for use with the fixed instrument guide device 1700. Next, driver tip 718 may be inserted into a socket of the selected screw using downward pressure to secure the screw to driver tip 718. In some embodiments, the screw may be a hex-head screw, and driver tip 718 may be a hex driver tip 718. Driver 706 and the screw are positioned in instrument guide tube 1710, and the screw tip is inserted into the previously drilled and/or tapped bone hole. Driver 706 is rotated, for example, clockwise to advance the screw until it is firmly seated. According to some embodiments of the present invention, the entire screw may be inserted into and through instrument guide tube 1710, through bone screw receiving hole 202, and into the bone hole. FIG. 24 depicts a fixed-type bone screw 1102 and driver 706 inserted through instrument guide tube 1710. In some cases, final adjustments may be necessary once fixed instrument guide device 1700 is removed from cervical plate 200. According to some embodiments of the present invention, depth stop line 720 becomes approximately level with the top of depth stop collar 1712 of instrument guide tube 1710 to indicate that the screw is nearly seated. A similar procedure may then be repeated for drilling, tapping, and placing a bone screw through the other bone screw receiving hole 202.

Figure 25:
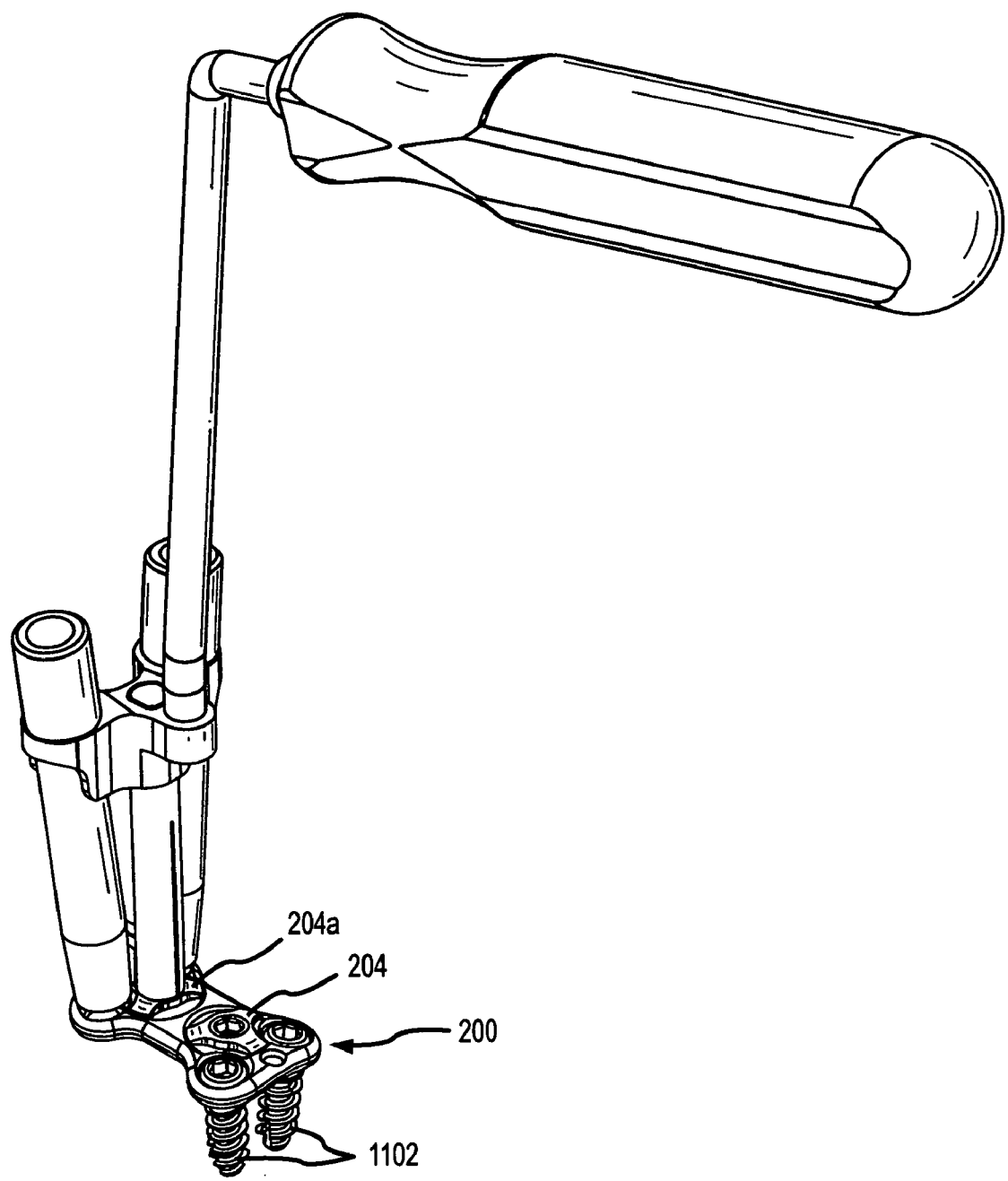
FIG. 25 illustrates a procedure for repositioning an embodiment of the instrument guide device of FIG. 17 on a cervical plate according to some embodiments of the present invention.
Figure 26:
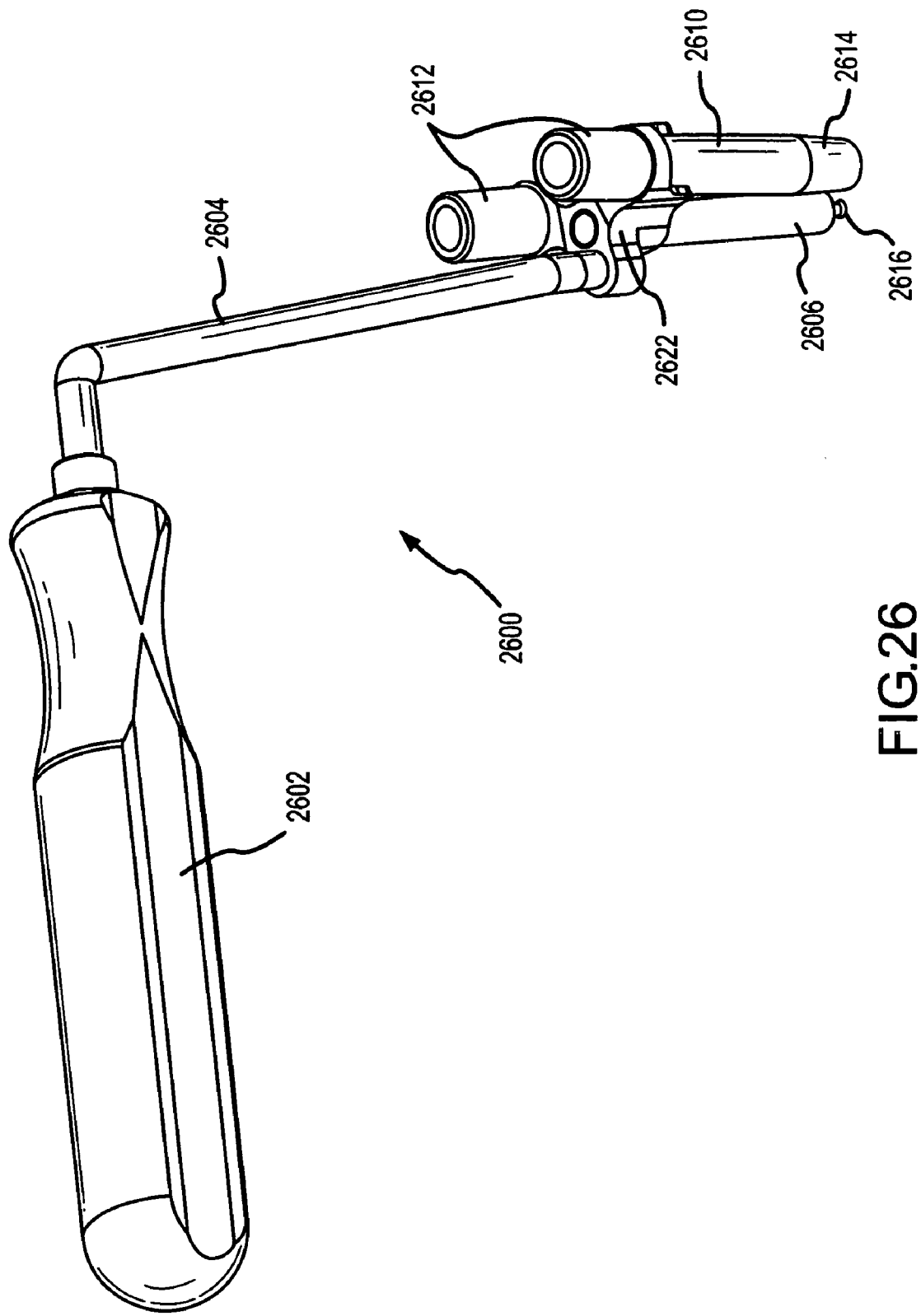
FIG. 26 illustrates an isometric view of an instrument guide device having a variable double instrument guide tube configuration according to some embodiments of the present invention.

FIG. 25 illustrates a procedure for repositioning instrument guide device 1700 on cervical plate 200 according to some embodiments of the present invention. Once bone screws have been placed through bone screw receiving holes 202 of one side of cervical plate 200, alignment stand 1706 of instrument guide device 1700 may be lifted from locking cap 204 (or other receptacle, as described above) and inserted into locking cap 204a (or other receptacle, as described above) of cervical plate 200 for placement of bone screws through remaining bone screw receiving holes 202. FIG. 25 illustrates such a procedure for cervical plate 200 through which two fixed-type bone screws 1102 have been placed on one side of cervical plate 200.

Figure 27A:
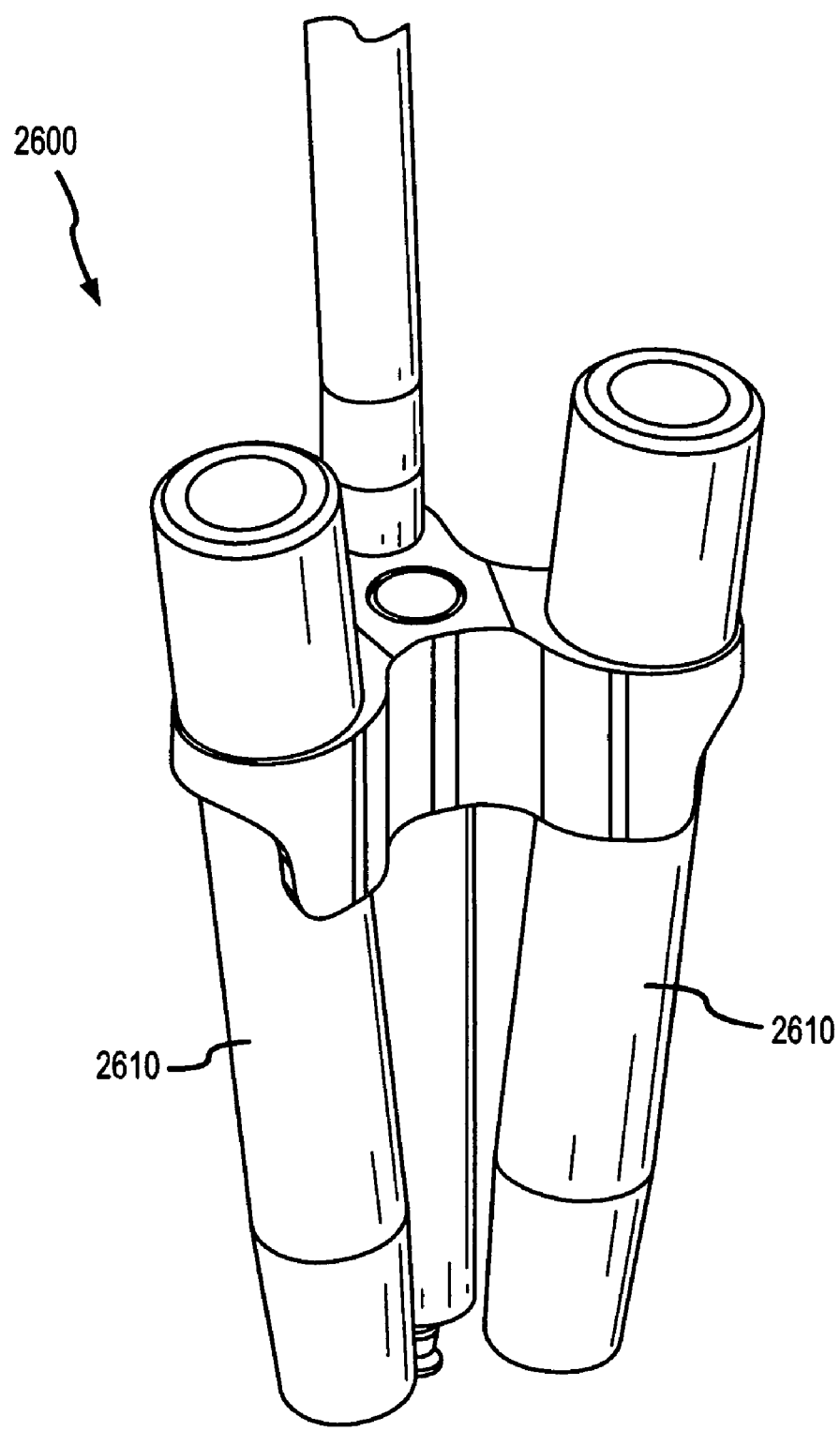
FIG. 27A illustrates an isometric view of an embodiment of the instrument guide device of FIG. 26 according to some embodiments of the present invention.
Figure 27B:
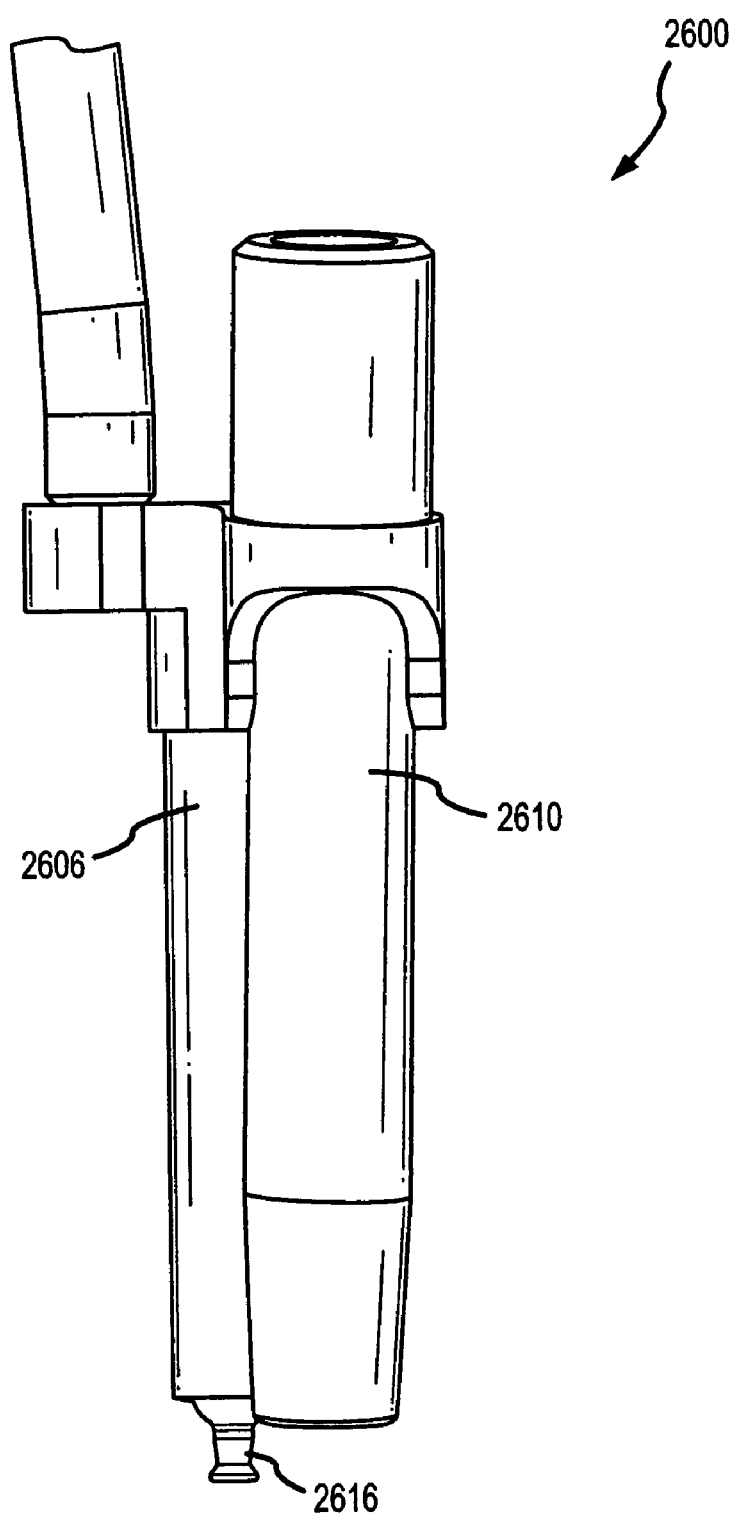
FIG. 27B illustrates a side perspective view of an embodiment of the instrument guide device of FIG. 26 according to some embodiments of the present invention.

Turning now to FIGS. 26, 27A, 27B, and 2, an instrument guide device 1700 having two fixed instrument guide tubes and cervical plate 200 according to some embodiments of the present invention are illustrated. Instrument guide device 2600 includes a handle 2602 and a handle shaft 2604 for holding instrument guide device 2600. According to some embodiments of the present invention, handle 2602 may be removable from handle shaft 2604. A brace portion 2622 is attached to handle shaft 2604, and an alignment stand 2606 is attached to brace portion 2622 and configured to interface a receptacle in cervical plate 200 via angle-limiting post 2616. For example, in some embodiments, alignment stand 2606 can interface with a locking cap 204 of cervical plate 200, as discussed in more detail above. According to some embodiments of the present invention, angle-limiting post 2616 is configured similarly to angle-limiting post 116. Hollow instrument guide tubes 2610 are affixed to brace portion 2622. In addition, instrument guide tube 2610 can include a depth stop collar 2612 at a top end for contacting and stopping instruments that have been inserted a predetermined depth into instrument guide tube 2610. Instrument guide tube 2610 can also include a tapered end 2614. FIG. 27A illustrates an isometric view, and FIG. 27B illustrates a side perspective view, of instrument guide device 2600 according to some embodiments of the present invention.

Figure 28:
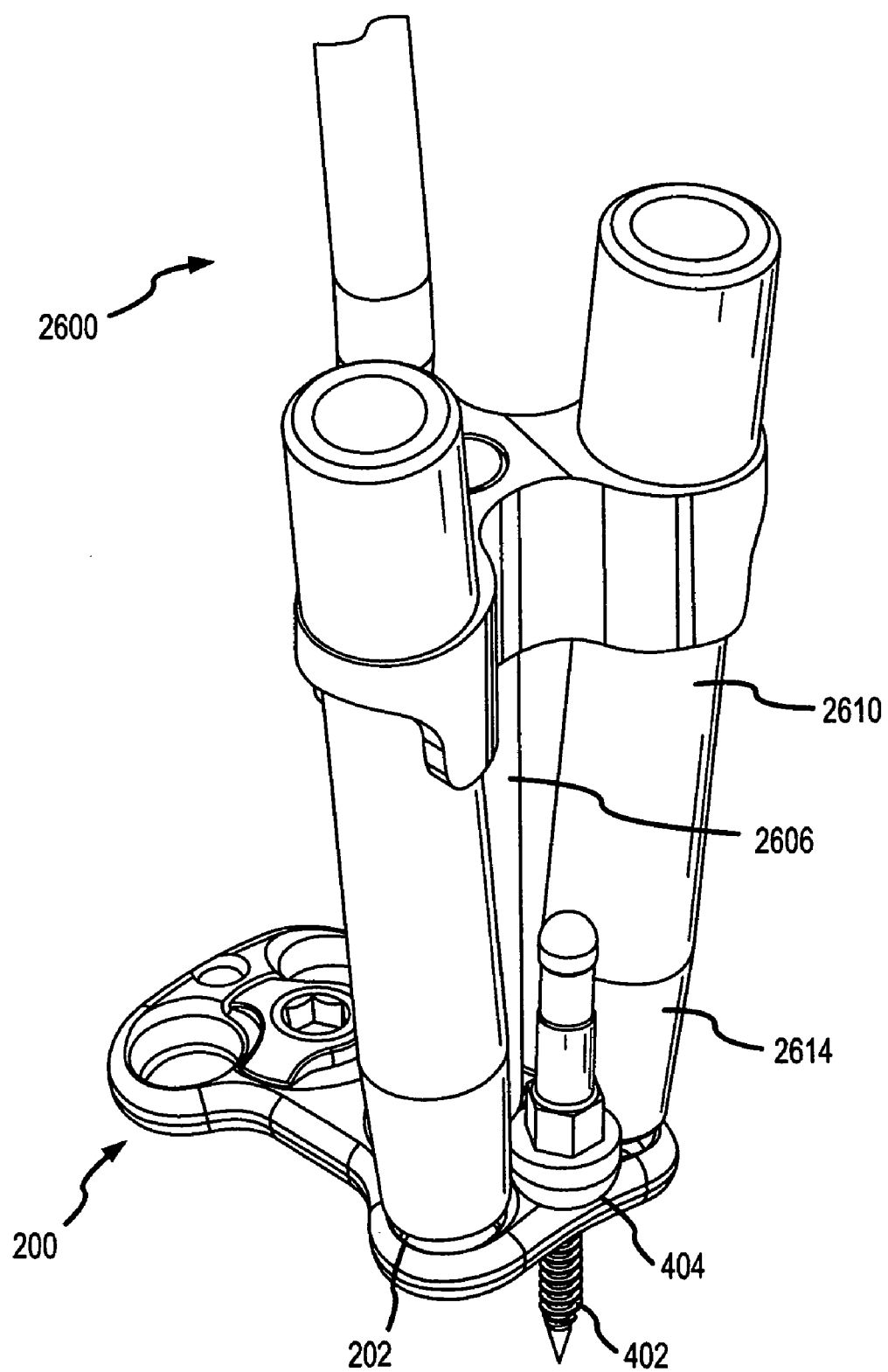
FIG. 28 illustrates an isometric view of an embodiment of the instrument guide device of FIG. 26 placed onto an embodiment of a cervical plate according to some embodiments of the present invention.
Figure 29:
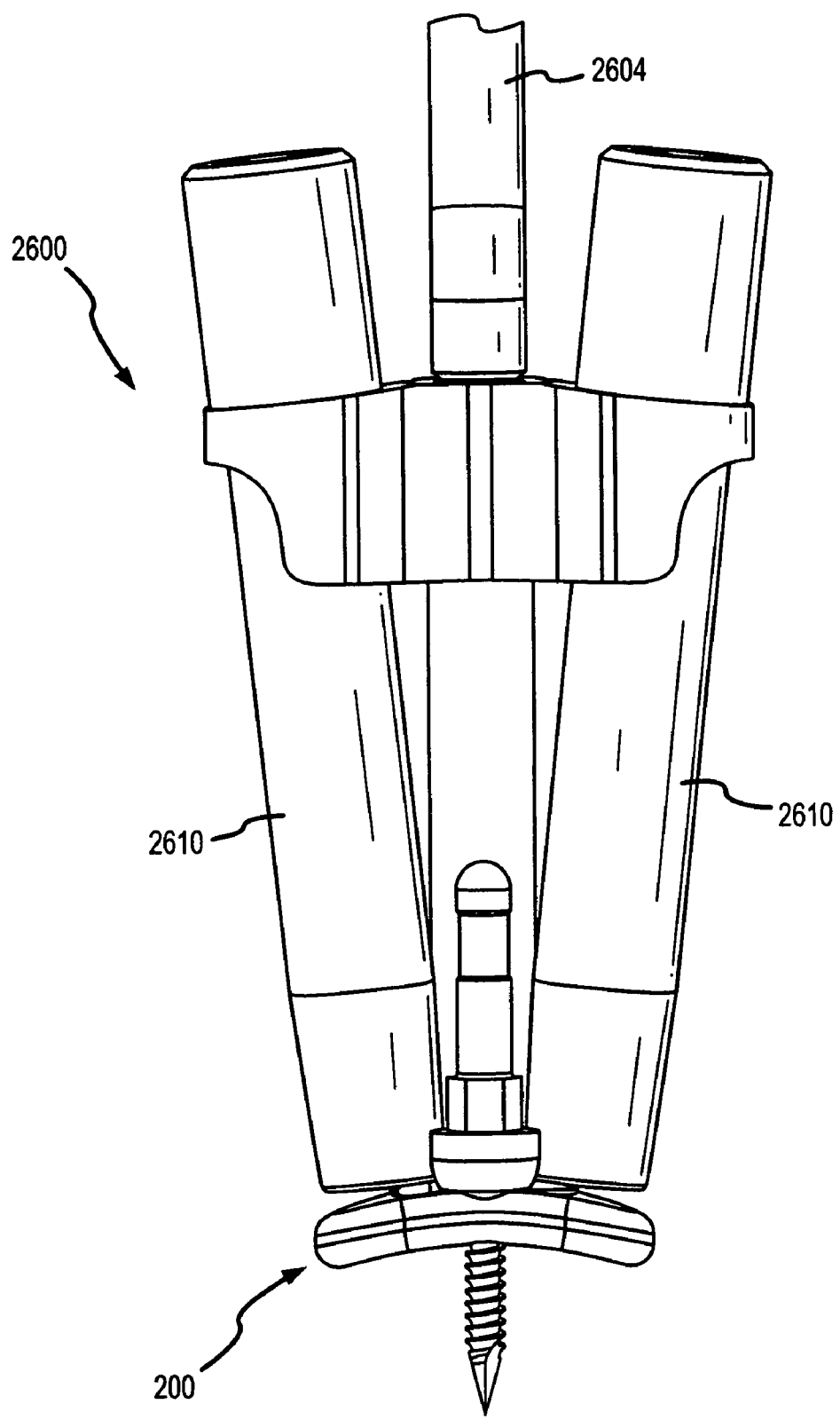
FIG. 29 illustrates a front perspective view of the configuration of FIG. 28.
Figure 30:
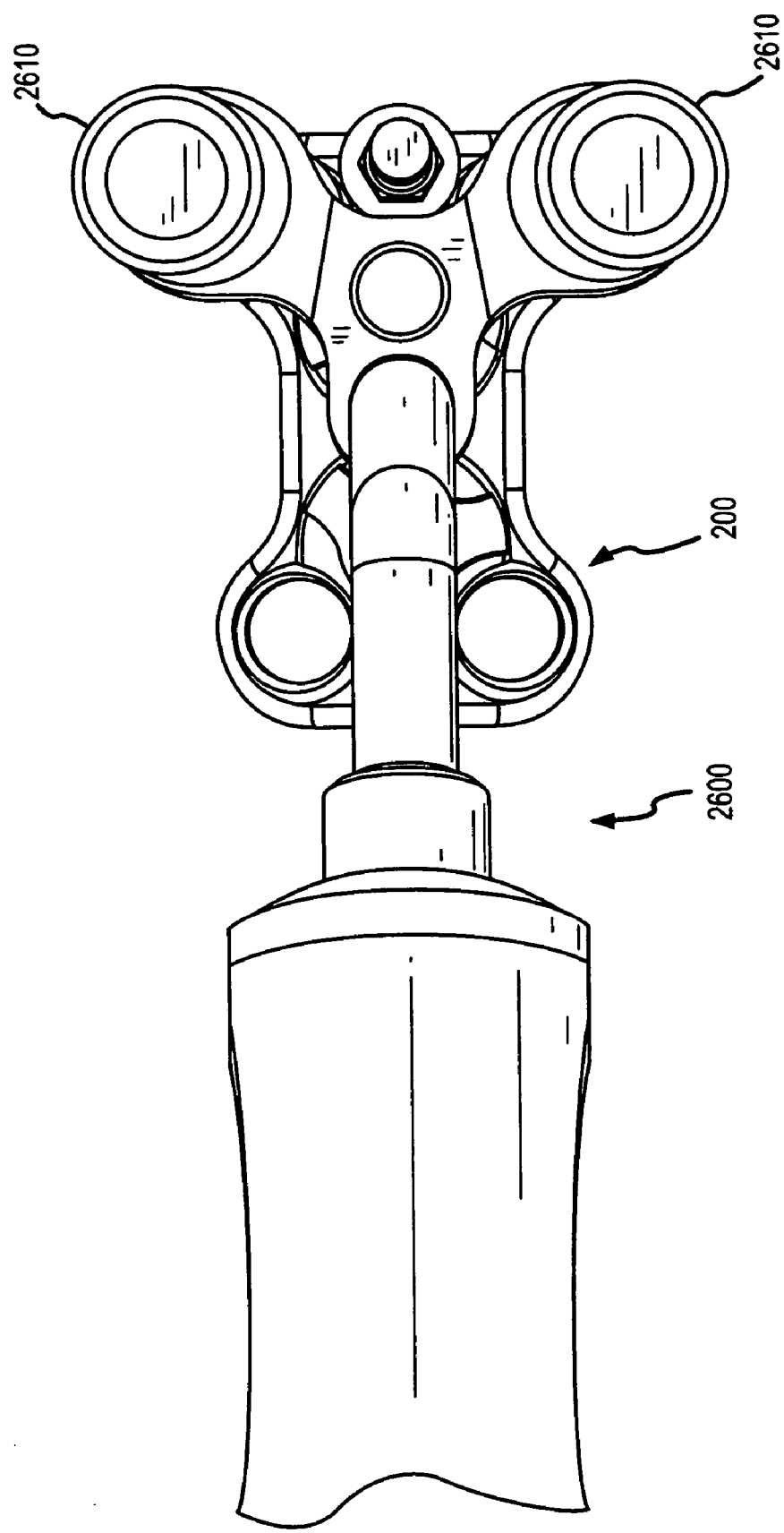
FIG. 30 illustrates top perspective view of the configurations of FIGS. 28 and 29.
Figure 31:
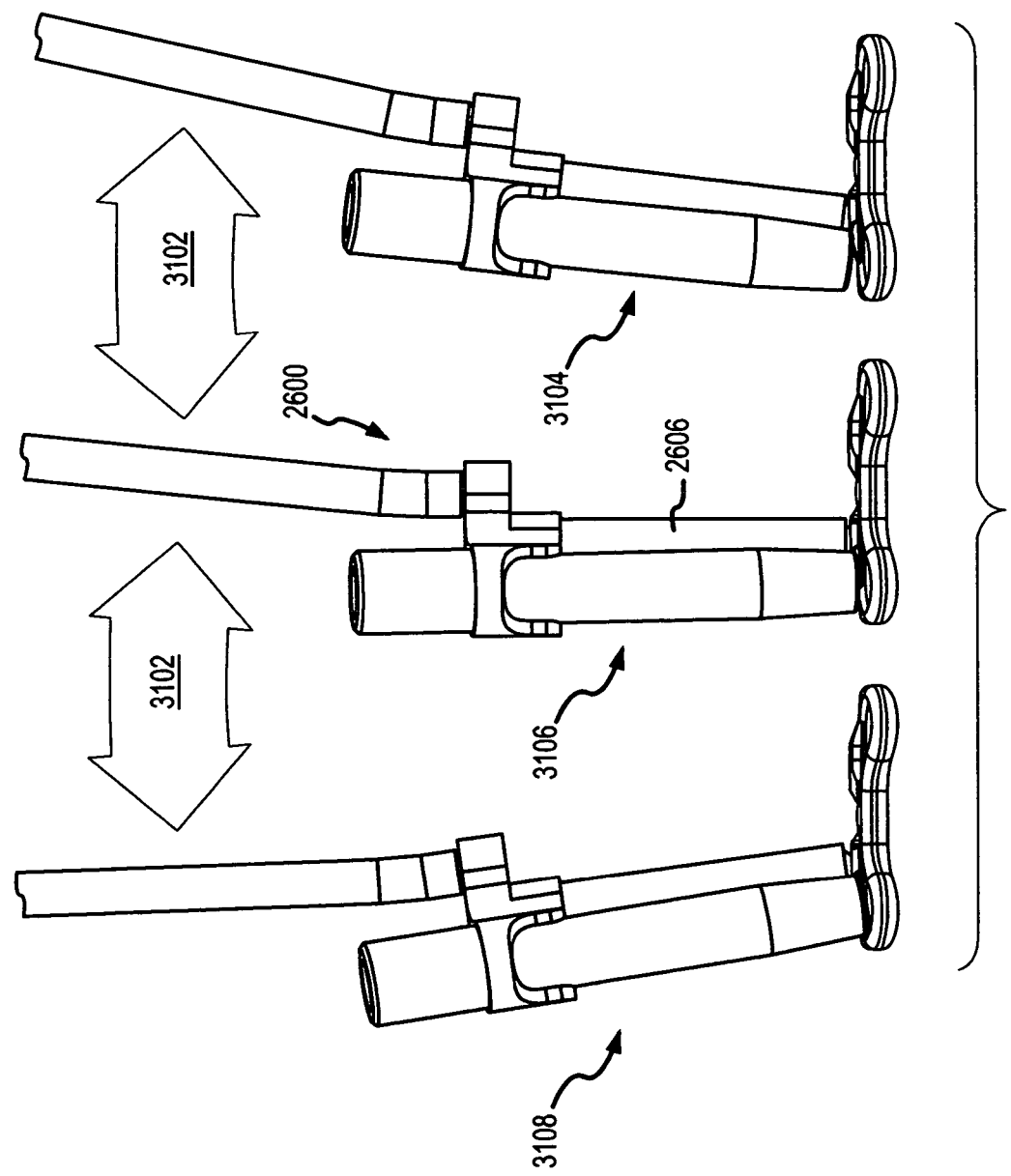
FIG. 31 illustrates side perspective views of embodiments of the instrument guide devices of FIG. 26 tilted at different angles with respect to a cervical plate according to various embodiments of the present invention.

In a common scenario, a cervical plate 200 of an appropriate size is selected for fixation to vertebral bodies. A properly sized plate 200 bridges affected segment(s) without overhanging into the adjacent disc space(s). Cervical plate 200 is positioned on the midline of the vertebral bodies. Referring now to FIGS. 28-30, a fixation pin 402 may be applied through a fixation hole 404 formed within cervical plate 200; fixation pin 402 may operate to hold cervical plate 200 in place during the fixation process: i.e., during drilling, tapping, and/or screwing. For example, fixation pin 402 may be used to hold cervical plate 200 positioned on midline of vertebral bodies during drilling and tapping of the first hole and/or application of the first bone screw through bone screw receiving hole 202 and into the first hole. According to some embodiments of the present invention, fixation pin 402 is used only temporarily to hold cervical plate 200 in place.

Once cervical plate 200 is positioned properly, angle-limiting post 2616 of instrument guide device 2600 is inserted into hex hole 206 of locking cap portion 204 of cervical plate 200. Handle shaft 2604 is then aligned approximately over the midline of cervical plate 200, as depicted in FIGS. 29 and 30, to avoid drilling or placing screws too far medially or laterally. When alignment stand 2606 has been inserted into locking cap portion 204, each instrument guide tube 2610 is positioned over a bone screw receiving hole 202 and an axial center line of each instrument guide tube 2610 passes through a bone screw receiving hole 202, as depicted, for example, in FIGS. 28-30. Tapered end 2614 of instrument guide tube 2610 may hover over bone screw receiving hole 202; alternatively, tapered end 2614 of instrument guide tube 2610 may fit on or within bone screw receiving hole 202 when angle-limiting post 2616 is inserted into hex hole 206. Alternatively, end 2614 may be non-tapered and/or flared. In addition, while the present embodiment has been described with reference to angle-limiting post 2616 being positioned within hex hole 206 of locking cap portion 204, the present invention is not limited to this embodiment. In alternative embodiments, cervical plate 200 might include an alternative receptacle for receiving angle-limiting post 2616.

Once instrument guide device 2600 has been positioned onto cervical plate 200, instrument guide device 2600 may be tilted to vary the screw placement angle. Instrument guide device 2600 is in a neutral position 3106 when alignment stand 2606 is vertical with respect to cervical plate 200, as illustrated by the side perspective view of FIG. 31. Instrument guide device 2600 may be tilted in one direction to a cephalad position 3104, or in the opposite direction to a caudad position 3108, as illustrated by arrows 3102. When instrument guide device 2600 has been tilted a certain angle into the cephalad position 3104, or a certain angle into the caudad position 3108, angle-limiting post 2616 abuts an inner surface of hex hole 206 of locking cap 204 (or an inner surface of an other receptacle, as discussed above) to prevent further tilting of instrument guide device 2600. In this way, angle-limiting post 2616 of alignment stand 2606 may be configured to allow only a recommended range of tilting angles, for example, twelve degrees in the caudad position 3108 to twelve degrees in the cephalad position 3104. Allowing a user to select a precise screw placement angle, such as a cephalad angle, a neutral angle, or a caudad angle, from a range of tilt angles may permit screw placement to be customized for a particular patient's anatomy or a particular surgical procedure. In some cases, a slightly cephalad position 3104 may be preferred for screw placement.

Figure 32:
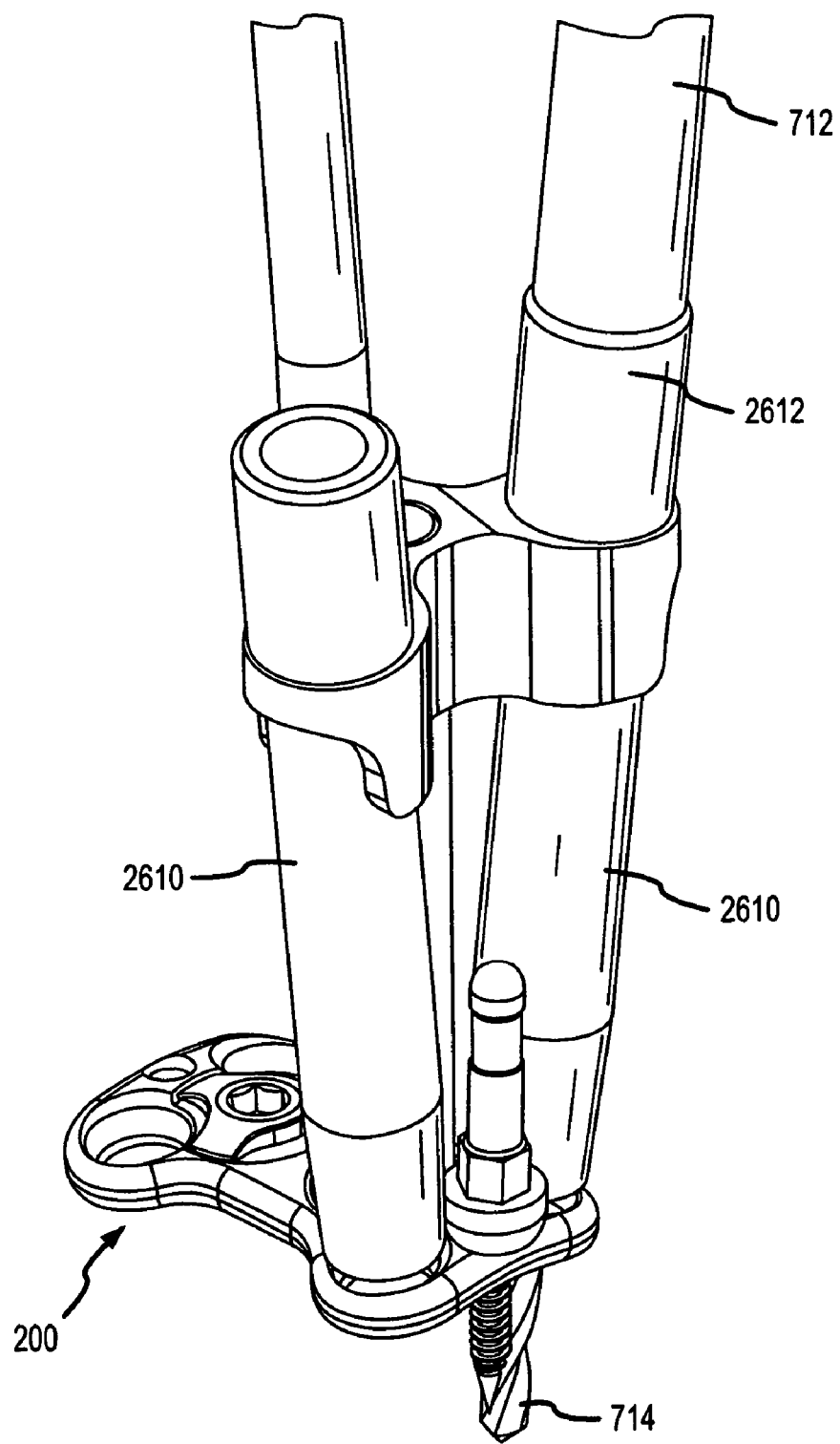
FIG. 32 illustrates an isometric view of an embodiment of the instrument guide device of FIG. 26 placed onto an embodiment of a cervical plate, with a drill inserted through one of the instrument guide tubes according to some embodiments of the present invention.

When a desired screw placement angle has been selected, drill bit 714 is inserted into instrument guide tube 2610, as illustrated in FIG. 32. Drill bit 714 is advanced, for example, in a clockwise rotational motion until the bottom 712 of depth stop collar 710 contacts the top of depth stop collar 2612 on instrument guide tube 2610. This will cause a hole to be drilled into the bone under cervical plate 200; drill bit 714 may also be rotated, for example, in a clockwise rotation when removed from the bone hole and instrument guide tube 2610. As one skilled in the art will appreciate based on the disclosure provided herein, the depth of the bone hole drilled corresponds to the placement of depth stop collar 2612 on instrument guide tube 2610 and depth stop collar 712 on drill 702. According to some embodiments of the present invention, a bone hole is drilled approximately twelve millimeters deep before depth stop collar 712 contacts depth stop collar 2612.

Figure 33:
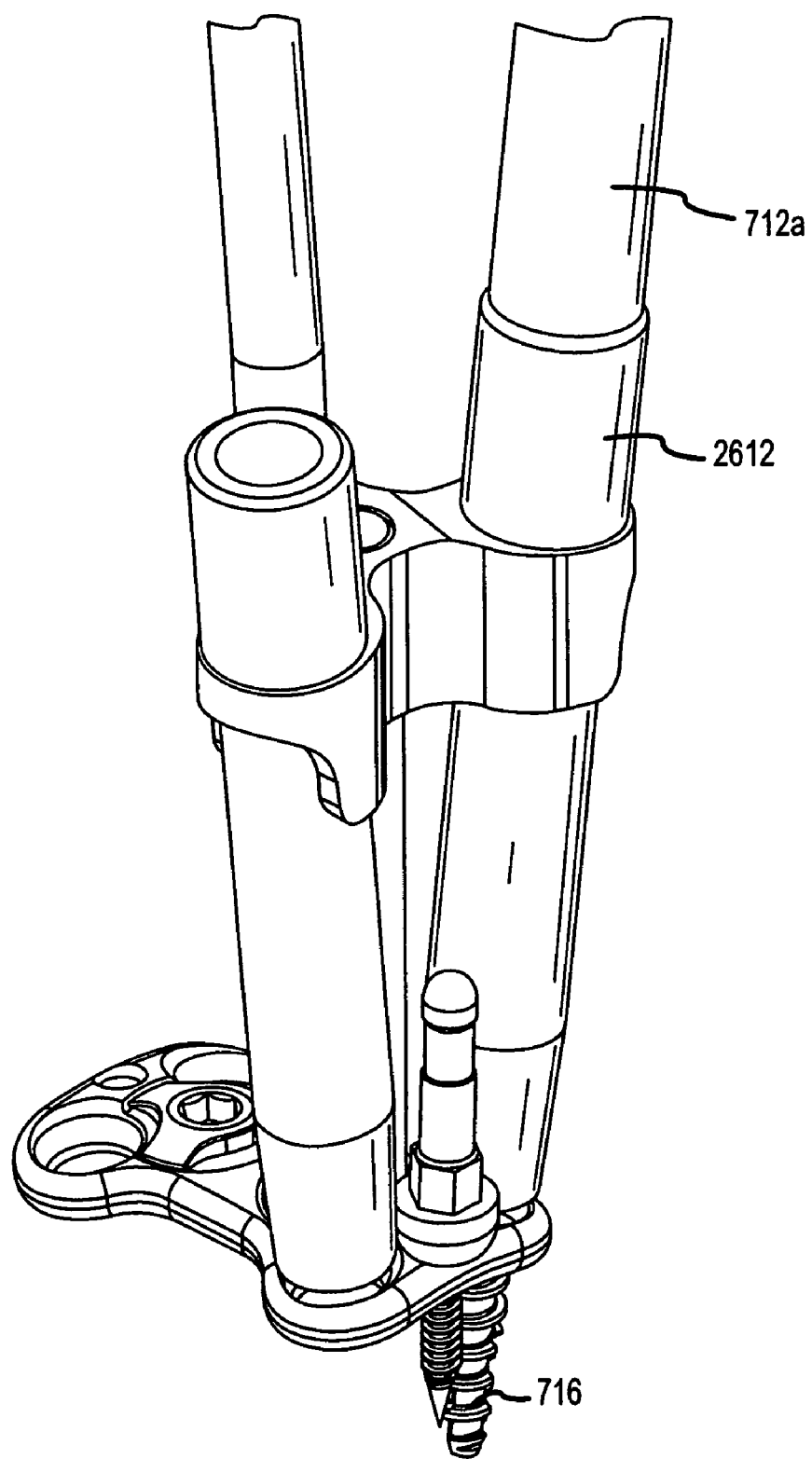
FIG. 33 illustrates an isometric view of an embodiment of the instrument guide device of FIG. 26 placed onto an embodiment of a cervical plate, with a tapping tool inserted through one of the instrument guide tubes according to some embodiments of the present invention.

Once a bone hole has been drilled, tap bit 716 may be inserted into instrument guide tube 2610 and into the previously drilled bone hole, as illustrated in FIG. 33. Tap 704 may be advanced, for example, in a clockwise rotational motion until the bottom 712a of depth stop collar 710a contacts the top of depth stop collar 2612 on instrument guide tube 2610. Once such contact is obtained, the bone hole has been tapped and tap 704 may be rotated, for example, counter-clockwise, until it is free of the bone hole, and removed from instrument guide tube 2610. According to some embodiments of the present invention, tapping the drilled hole prior to screw placement is an optional step.

Figure 34:
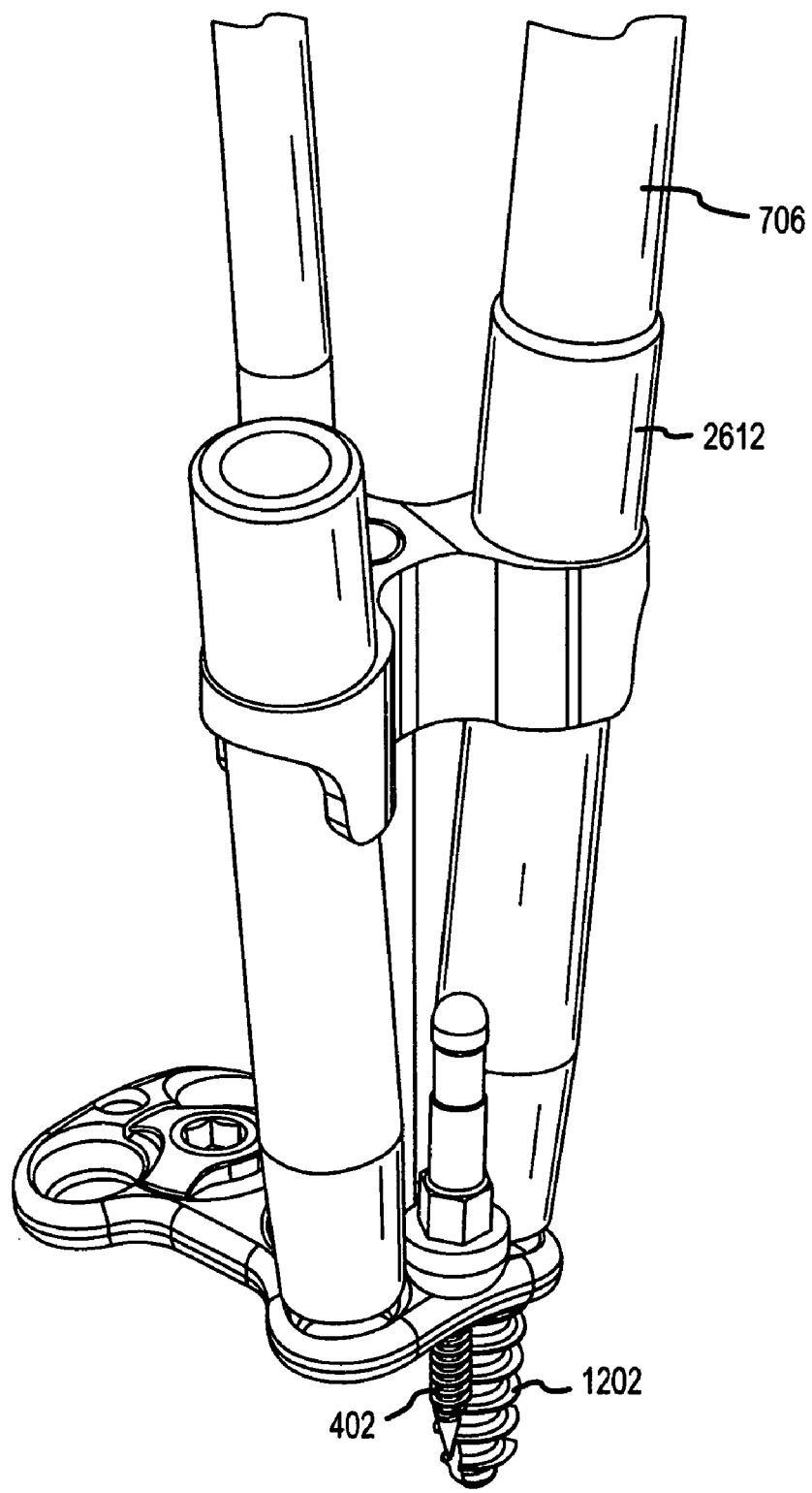
FIG. 34 illustrates an isometric view of an embodiment of the instrument guide device of FIG. 26 placed onto an embodiment of a cervical plate, with a variable-type screw and screw driver inserted through one of the instrument guide tubes according to some embodiments of the present invention.

When a bone hole has been drilled and tapped, a correct type of screw is selected. The screw type may be fixed or variable. A variable-type screw is selected for double instrument guide tube variable instrument guide device 2600. Next, driver tip 718 may be inserted into a socket of the selected screw using downward pressure to secure the screw to driver tip 718. The screw may be a hex-head screw, and driver tip 718 may be a hex driver tip 718. Driver 706 and the screw are positioned in instrument guide tube 2610, and the screw tip is inserted into the previously drilled and/or tapped bone hole. Driver 706 is rotated, for example, clockwise to advance the screw until it is firmly seated. According to some embodiments of the present invention, the entire screw may be inserted into and through instrument guide tube 2610, through bone screw receiving hole 202, and into the bone hole. FIG. 34 depicts a variable-type bone screw 1202 and driver 706 inserted through instrument guide tube 2610. In some cases, final adjustments may be necessary once fixation pin 402 is removed from cervical plate 200. According to some embodiments of the present invention, depth stop line 720 becomes approximately level with the top of depth stop collar 2612 of instrument guide tube 2610 to indicate that the screw is nearly seated. A similar procedure may then be repeated for drilling, tapping, and placing a bone screw through the other bone screw receiving hole 202.

Figure 35:
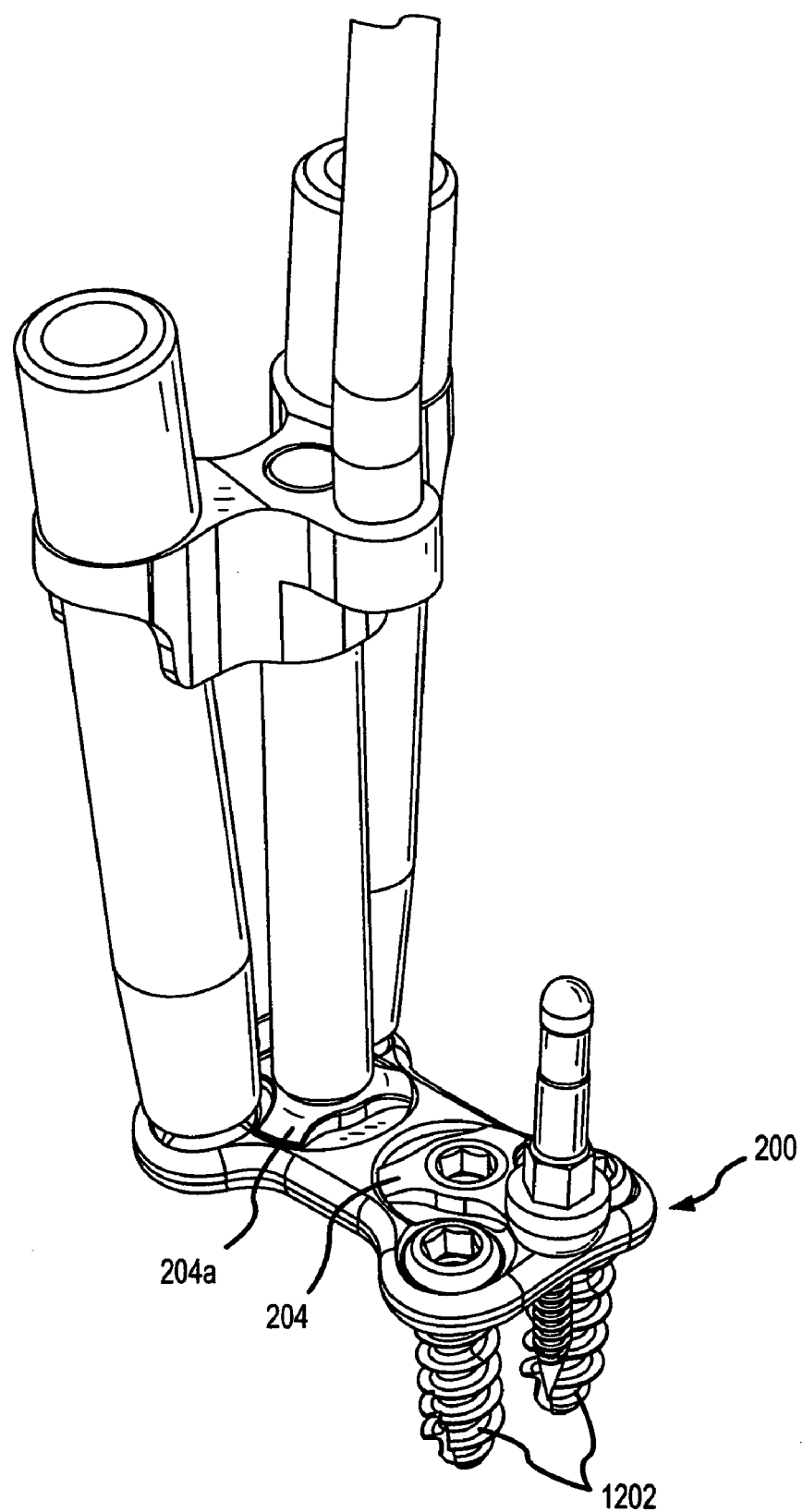
FIG. 35 illustrates a procedure for repositioning an embodiment of the instrument guide device of FIG. 26 on a cervical plate according to some embodiments of the present invention.

FIG. 35 illustrates a procedure for repositioning double instrument guide tube variable instrument guide device 2600 on cervical plate 200 according to some embodiments of the present invention. Once bone screws have been placed through bone screw receiving holes 202 of one side of cervical plate 200, alignment stand 2606 of instrument guide device 2600 may be lifted from locking cap 204 and inserted into locking cap 204*a* of cervical plate 200 for placement of bone screws through remaining bone screw receiving holes 202. FIG. 35 illustrates such a procedure for cervical plate 200 through which two variable-type bone screws 1202 have been placed on one side of cervical plate 200.

According to some embodiments of the present invention, a surgeon may select one or more of the following embodiments of the present invention for attaching a cervical plate 200 to underlying vertebrae: instrument guide device 100 having a swiveling single instrument tube, instrument guide device 1700 having two fixed instrument guide tubes, and instrument guide device 2600 having two fixed instrument guide tubes. Alignment posts 106, 1706, and/or 2606 permit greater stability and precision by at least partially eliminating the need for instrument guide tubes 110, 1710, or 2610 themselves to rest on cervical plate 200. Use of instrument guide device 100 having a swiveling single instrument guide tube may permit a smaller incision to be made for cervical plating procedures, compared to multiple instrument guide tube instrument guides. The swiveling capability of instrument guide device 100 and instrument guide device 2600 may also allow a surgeon to place bone screws at different angles to customize a particular screw placement to a particular patient's anatomy. Use of instrument guide device 1700 may permit a greater degree of stability with stem 1718 inserted into hex hole 206 of locking cap 204 (or other receptacle, as described above), and bone pin 1720 may eliminate the need for provision and insertion of a separate fixation pin 402. Instrument guide device 1700 and instrument guide device 2600 can permit bone screws to be placed through both bone screw holes on the same side of cervical plate using the same instrument guide device; this may eliminate the need to use a separate instrument guide device for each bone screw receiving hole and may shorten cervical plating procedures by minimizing the need to place and replace numerous instrument guide devices for the same side of the cervical plate 200. Embodiments of the present invention can also permit both a screw and driver to be inserted through the instrument guide tube 110, 1710, or 2610, eliminating the need to remove the instrument guide device before placing the screw.

Embodiments of the invention have now been described in detail for purposes of clarity and understanding. However, it will be appreciated that certain changes and modifications may be practiced within the scope of the appended claims. Thus, although the invention is described with reference to specific embodiments and figures thereof, the embodiments and figures are merely illustrative, and not limiting of the invention. Rather, the scope of the invention is to be determined solely by the appended claims.

What is claimed is:

1. An apparatus for guiding medical instruments used in attaching a cervical plate, the cervical plate having a receptacle, the apparatus comprising:
   a handle comprising a handle shaft;
   an alignment stand affixed to the handle shaft and configured to interface with the receptacle, wherein a first end of the alignment stand comprises an angle-limiting post, the angle limiting post having a neck portion and a flared distal end, the angle-limiting post configured to be seated within the receptacle to permit the alignment stand to interface with the receptacle at a range of angles such that when the angle-limiting post is seated in the receptacle, the alignment stand can be tilted relative to the cervical plate through the range of angles, and wherein the flared distal end of the angle-limiting post is configured to limit the angle by abutting the receptacle when the angle equals a maximum angle; and
   an instrument guide tube coupled to the alignment stand and having a lumen therethrough;
   wherein when the first end of the alignment stand is in communication with the receptacle in the cervical plate, the instrument guide tube is positioned over a bone screw receiving hole in the cervical plate and an axial centerline of the instrument guide tube passes through the bone screw receiving hole.

2. The apparatus of claim 1, wherein the instrument guide tube comprises a first end and a second end, and wherein the first end of the instrument guide tube includes a depth stop collar.

3. The apparatus of claim 2, wherein the second end of the instrument guide tube is tapered.

4. The apparatus of claim 1, wherein the cervical plate comprises a locking cap which acts as the receptacle.

5. The apparatus of claim 1, wherein the instrument guide tube is coupled to a second end of the alignment stand.

6. The apparatus of claim 1, wherein the instrument guide tube can swivel about the alignment stand so that the instrument guide tube can be positioned over a second bone screw receiving hole in the cervical plate.

7. The apparatus of claim 1, wherein the instrument guide tube is a first instrument guide tube, and wherein the bone screw receiving hole is a first bone screw receiving hole, the apparatus further comprising:
   a second instrument guide tube coupled to the alignment stand and including a lumen therethrough;
   wherein the alignment stand is configured to interface with the receptacle of the cervical plate, such that when the first end of the alignment stand is in communication with the receptacle in the cervical plate, the second instrument guide tube is positioned over a second bone screw receiving hole in the cervical plate and an axial centerline of the second instrument guide tube passes through the second bone screw receiving hole.

8. An apparatus for guiding medical instruments used in attaching a cervical plate, the cervical plate having a receptacle, the apparatus comprising:
a handle comprising a handle shaft;
an alignment stand affixed to the handle shaft and configured to interface with the receptacle, the alignment stand including at least two alignment slots formed therein, wherein a first end of the alignment stand comprises an angle-limiting post having a ball portion configured to be seated within the receptacle, wherein the ball portion is configured to roll or tilt within the receptacle to permit the alignment stand to interface with the receptacle at a range of angles, and wherein the angle-limiting post is configured to allow the alignment stand to be tilted through the range of angles while the angle-limiting post is seated in the receptacle, and to limit the angle by abutting the receptacle when the angle equals a maximum angle; and
an instrument guide tube comprising a lumen therethrough and a rotational coupling operable to rotatably couple the instrument guide tube to the alignment stand, the rotational coupling comprising an alignment pin operable to seat in one of the at least two alignment slots to prevent the instrument guide tube from rotating about the alignment stand;
wherein when a first end of the alignment stand is in communication with the receptacle in the cervical plate and the alignment pin is seated in one of the at least two alignment slots, the instrument guide tube is positioned over a bone screw receiving hole in the cervical plate and an axial centerline of the instrument guide tube passes through the bone screw receiving hole.

9. The apparatus of claim 8, wherein:
the alignment stand comprises a first annular ring and a second annular ring and the at least two alignment slots are formed in the first annular ring;
rotational coupling of the instrument guide tube comprises a rotational sleeve surrounding the first and the second annular rings of the alignment stand;
the alignment pin protrudes within the rotational sleeve between the first annular ring and the second annular ring; and
the rotational sleeve rotates with respect to the alignment stand unless the alignment pin is seated in one of the at least two alignment slots.

10. The apparatus of claim 9, wherein the rotational sleeve comprises a bottom collar, the apparatus further comprising:
a spring in compression between the first annular ring and the bottom collar, wherein compression pressure from the spring is operable to hold the alignment pin in the one of the at least two alignment slots, and wherein the spring is operable to further compress as the rotational sleeve is lifted and rotated to permit the alignment pin to seat in another of the at least two alignment slots.

11. The apparatus of claim 8, wherein the instrument guide tube comprises a first end and a second end, and wherein the first end of the instrument guide tube comprises a depth stop collar.

12. The apparatus of claim 11, wherein the second end of the instrument guide tube is tapered.

* * * * *